(12) United States Patent
Bierman et al.

(10) Patent No.: US 7,568,484 B2
(45) Date of Patent: Aug. 4, 2009

(54) ENDO-TRACHEAL TUBE SECUREMENT SYSTEM

(75) Inventors: Steven F. Bierman, Del Mar, CA (US); Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 134 days.

(21) Appl. No.: 11/303,454

(22) Filed: Dec. 16, 2005

(65) Prior Publication Data

US 2006/0124133 A1  Jun. 15, 2006

Related U.S. Application Data

(63) Continuation-in-part of application No. 11/194,975, filed on Aug. 2, 2005, which is a continuation of application No. 10/826,689, filed on Apr. 16, 2004, now Pat. No. 6,948,500, which is a continuation-in-part of application No. 10/270,883, filed on Oct. 11, 2002, now Pat. No. 6,796,310.

(60) Provisional application No. 60/718,574, filed on Sep. 19, 2005, provisional application No. 60/328,727, filed on Oct. 11, 2001.

(51) Int. Cl.
*A61M 11/00* (2006.01)
(52) U.S. Cl. .............................. 128/207.17; 128/206.27
(58) Field of Classification Search ............ 128/207.17, 128/207.11, 206.27, DIG. 26, 202.18, 857, 128/859–871, 845, 202.28, 202.29, 203.11, 128/911, 912, 202.27, 908, 207.29; 602/17, 602/18, 74; 601/40–44; 600/21, 22; 5/636–639
See application file for complete search history.

(56) References Cited

U.S. PATENT DOCUMENTS

| 250,567 | A | 12/1881 | Bennett |
| 2,507,617 | A | 5/1950 | Swendiman |
| 3,013,556 | A | 12/1961 | Galleher, Jr. |
| 3,046,989 | A | 7/1962 | Hill |
| 3,461,858 | A | 8/1969 | Michelson |

(Continued)

FOREIGN PATENT DOCUMENTS

WO    WO 03/030976    4/2003

OTHER PUBLICATIONS

Invitation to Pay Additional Search Fees, PCT Application No. PCT/US2006/048076, mailed Jun. 12, 2007, 8 pages.
Office Action in U.S. Appl. No. 11/194,975, dated Feb. 13, 2009.

*Primary Examiner*—Steven O Douglas
(74) *Attorney, Agent, or Firm*—Knobbe Martens Olson & Bear LLP

(57) ABSTRACT

A system for securing an endo-tracheal tube or other medical article in position upon a patient includes a head contact member, retainer, and attachment members which can be adjustably attached between the head contact member and the retainer. Certain embodiments of the head contact member have a concave shape which follows a portion of the patient's skull and may have a rigid or flexible structure. In certain embodiments, a flexible head contact member includes straps forming a closed loop. In certain embodiment, the attachment members are integral to one or both of the head contact member and the retainer. The attachment member attaches to the retainer which grips the endo-tracheal tube or other medical article.

23 Claims, 32 Drawing Sheets

U.S. PATENT DOCUMENTS

| | | | |
|---|---|---|---|
| 3,482,571 A | 12/1969 | Behrendt | |
| 3,602,227 A | 8/1971 | Andrew | |
| 3,629,032 A | 12/1971 | Erb | |
| 3,760,811 A | 9/1973 | Andrew | |
| 4,062,357 A * | 12/1977 | Laerdal | 128/206.26 |
| 4,114,626 A | 9/1978 | Beran | |
| 4,142,527 A | 3/1979 | Garcia | |
| 4,182,322 A | 1/1980 | Miller | |
| 4,249,529 A * | 2/1981 | Nestor et al. | 128/207.17 |
| 4,284,076 A | 8/1981 | Hall | |
| 4,297,999 A | 11/1981 | Kitrell | |
| 4,310,307 A | 1/1982 | Bellisario | |
| 4,331,143 A | 5/1982 | Foster | |
| 4,340,046 A | 7/1982 | Cox | |
| 4,351,331 A | 9/1982 | Gereg | |
| 4,367,735 A | 1/1983 | Dali | |
| 4,449,527 A | 5/1984 | Hinton | |
| 4,548,200 A | 10/1985 | Wapner | |
| 4,592,351 A | 6/1986 | Smith et al. | |
| 4,658,814 A | 4/1987 | Anderson | |
| 4,683,882 A | 8/1987 | Laird | |
| 4,744,358 A | 5/1988 | McGinnis | |
| 4,774,944 A | 10/1988 | Mischinski | |
| 4,821,736 A | 4/1989 | Watson | |
| 4,832,019 A | 5/1989 | Weinstein et al. | |
| 4,848,331 A | 7/1989 | Northway-Meyer | |
| 4,850,348 A | 7/1989 | Pell et al. | |
| 4,867,154 A | 9/1989 | Potter et al. | |
| 4,906,234 A | 3/1990 | Voychehovski | |
| 4,932,943 A | 6/1990 | Nowak | |
| 4,988,062 A | 1/1991 | London | |
| 4,991,272 A | 2/1991 | Bianchi | |
| 5,007,122 A | 4/1991 | Daughdrill | |
| 5,009,227 A | 4/1991 | Nieuwstad | |
| 5,038,778 A | 8/1991 | Lott | |
| 5,042,477 A | 8/1991 | Lewis | |
| 5,069,206 A | 12/1991 | Crosbie | |
| 5,076,269 A | 12/1991 | Austin | |
| 5,205,832 A | 4/1993 | Tuman | |
| 5,237,988 A | 8/1993 | McNeese | |
| 5,253,643 A | 10/1993 | Price | |
| 5,295,480 A | 3/1994 | Zemo | |
| 5,305,742 A | 4/1994 | Styers et al. | |
| 5,320,097 A | 6/1994 | Clemens et al. | |
| 5,345,931 A | 9/1994 | Battaglia, Jr. | |
| 5,357,952 A | 10/1994 | Schuster et al. | |
| 5,368,024 A | 11/1994 | Jones | |
| 5,383,451 A | 1/1995 | Delulio | |
| 5,387,177 A | 2/1995 | Dunn | |
| 5,398,679 A | 3/1995 | Freed | |
| 5,402,776 A | 4/1995 | Islava | |
| 5,411,484 A | 5/1995 | Shattuck | |
| 5,435,323 A | 7/1995 | Rudy | |
| 5,437,273 A | 8/1995 | Bates et al. | |
| 5,479,921 A | 1/1996 | Reif | |
| 5,488,944 A | 2/1996 | Kennedy | |
| 5,490,504 A | 2/1996 | Vrona et al. | |
| 5,507,285 A | 4/1996 | Mota | |
| 5,513,633 A | 5/1996 | Islava | |
| 5,515,867 A | 5/1996 | Lamb | |
| 5,517,986 A | 5/1996 | Starr et al. | |
| 5,531,229 A | 7/1996 | Dean et al. | |
| 5,551,421 A | 9/1996 | Noureldin et al. | |
| 5,555,881 A | 9/1996 | Rogers et al. | |
| 5,558,090 A | 9/1996 | James | |
| 5,570,689 A * | 11/1996 | Starr et al. | 128/207.11 |
| 5,626,565 A | 5/1997 | Landis et al. | |
| 5,638,814 A | 6/1997 | Byrd | |
| 5,649,534 A | 7/1997 | Briggs, II | |
| 5,653,232 A | 8/1997 | Rogers et al. | |
| 5,662,101 A | 9/1997 | Odgen et al. | |
| 5,672,159 A | 9/1997 | Warrick | |
| 5,743,885 A | 4/1998 | Hoerby | |
| 5,771,513 A | 6/1998 | Kirchgeorg et al. | |
| 5,803,079 A | 9/1998 | Rogers et al. | |
| 5,806,516 A | 9/1998 | Beattie | |
| 5,829,430 A | 11/1998 | Islava | |
| 5,839,437 A * | 11/1998 | Briggs, III | 128/207.17 |
| 5,918,599 A | 7/1999 | Shesol | |
| 5,924,421 A | 7/1999 | Rosbrook et al. | |
| 5,927,276 A | 7/1999 | Rodriguez | |
| 5,934,276 A | 8/1999 | Fabro et al. | |
| 5,967,144 A | 10/1999 | Reynolds | |
| 5,988,173 A | 11/1999 | Scruggs | |
| 5,996,581 A * | 12/1999 | Duch | 128/206.26 |
| 6,009,872 A | 1/2000 | Delaplane et al. | |
| 6,029,668 A | 2/2000 | Freed | |
| 6,050,263 A | 4/2000 | Choksi et al. | |
| 6,067,985 A | 5/2000 | Islava | |
| 6,081,925 A | 7/2000 | Reiber | |
| 6,336,457 B1 | 1/2002 | Hudson et al. | |
| 6,371,110 B1 * | 4/2002 | Peterson et al. | 128/202.27 |
| 6,422,238 B1 | 7/2002 | Lithgow | |
| 6,526,978 B2 * | 3/2003 | Dominguez | 128/207.14 |
| 6,578,576 B1 | 6/2003 | Taormina et al. | |
| 6,634,359 B1 * | 10/2003 | Rudy et al. | 128/207.14 |
| 6,736,139 B1 | 5/2004 | Wix | |
| 6,745,772 B1 * | 6/2004 | McLeod | 128/206.21 |
| 6,796,310 B2 | 9/2004 | Bierman | |
| 6,805,117 B1 * | 10/2004 | Ho et al. | 128/201.22 |
| 6,840,238 B1 | 1/2005 | Van Hegelsom | |
| 6,948,500 B2 | 9/2005 | Bierman | |
| 7,036,460 B2 | 5/2006 | Ducharme et al. | |
| 7,063,088 B1 | 6/2006 | Christopher | |
| 7,134,436 B2 * | 11/2006 | Frank | 128/846 |
| 7,165,380 B2 | 1/2007 | Oyster et al. | |
| 7,188,620 B2 * | 3/2007 | Amarasinghe | 128/201.22 |
| 7,195,018 B1 | 3/2007 | Goldstein | |
| 2004/0035428 A1 | 2/2004 | Olsen et al. | |
| 2004/0244799 A1 | 12/2004 | Landis | |
| 2005/0092328 A1 | 5/2005 | Herrick et al. | |
| 2005/0133038 A1 | 6/2005 | Rutter | |
| 2006/0118120 A1 * | 6/2006 | Russo | 128/207.14 |
| 2006/0174893 A1 * | 8/2006 | Kanowitz | 128/207.14 |

* cited by examiner

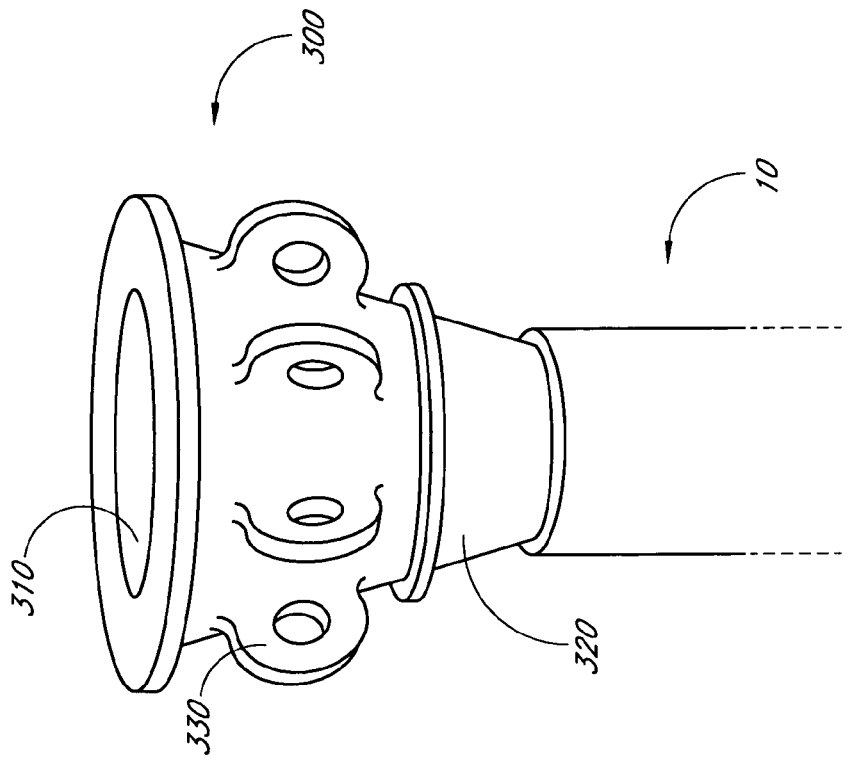
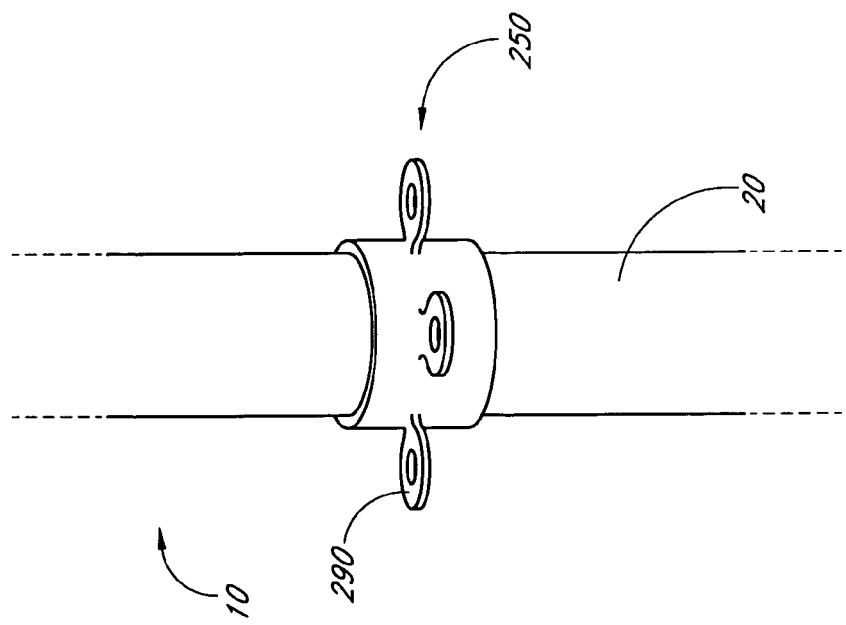

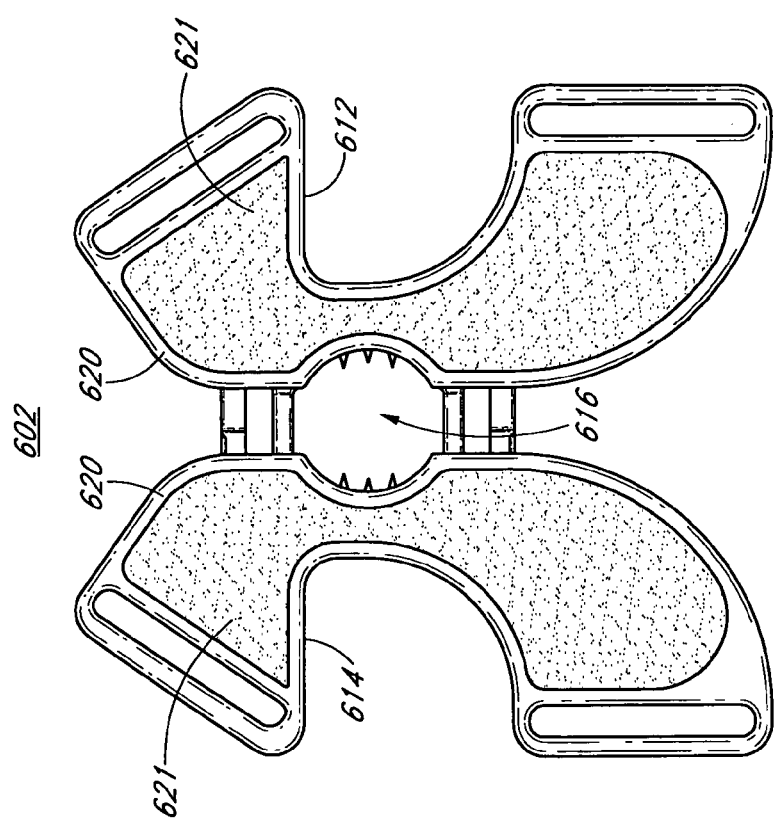
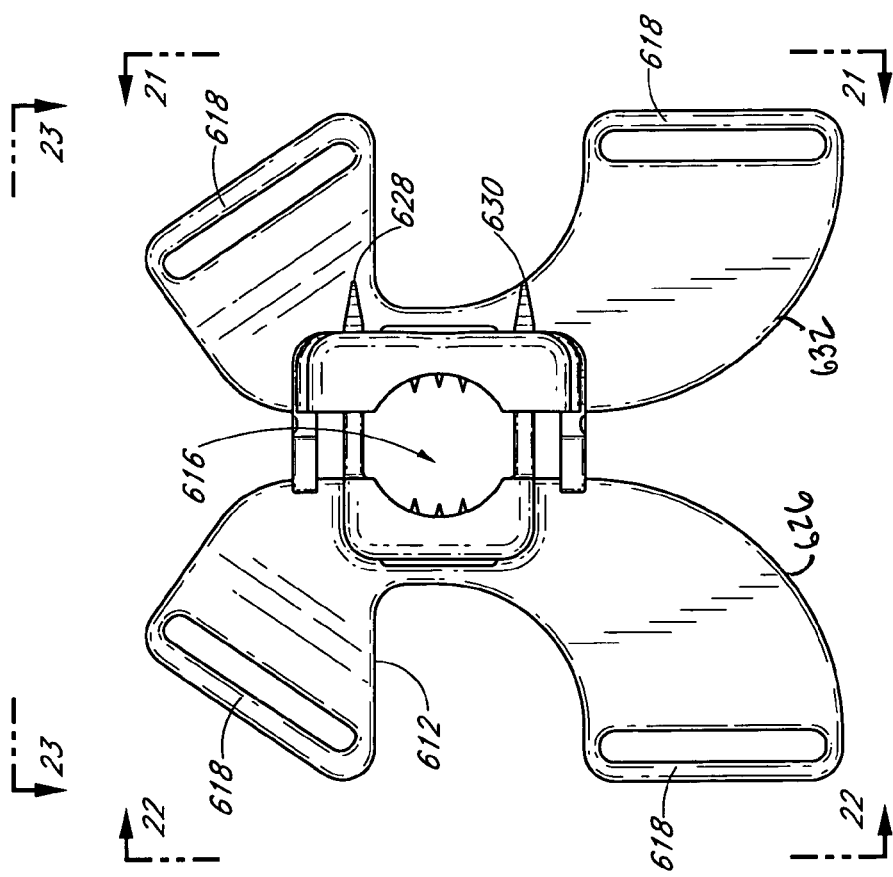
FIG. 20
FIG. 19

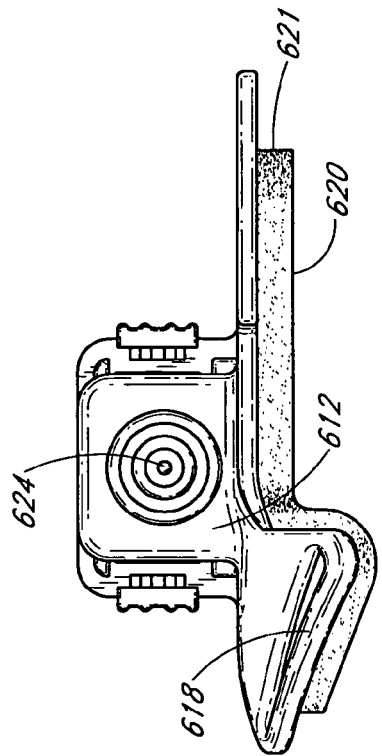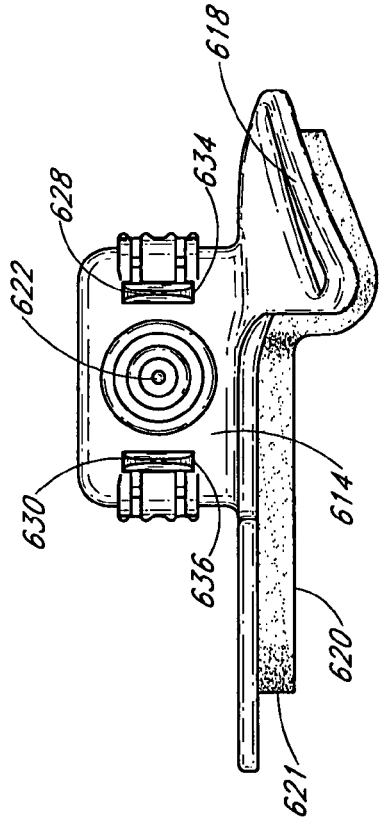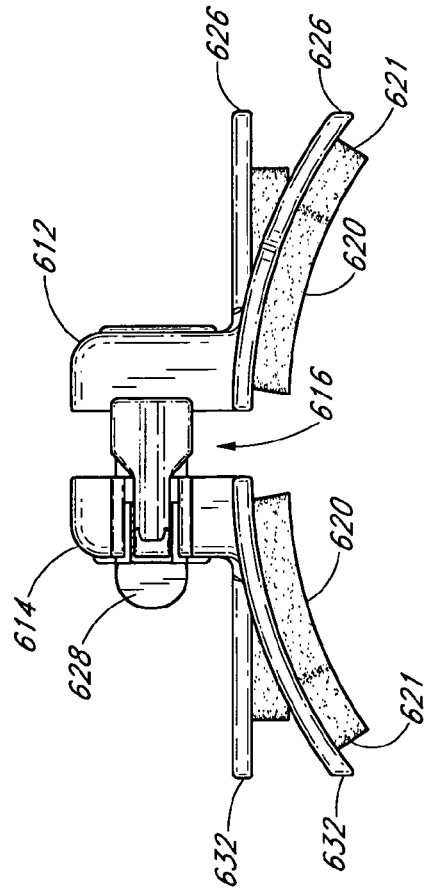
FIG. 22
FIG. 23
FIG. 21

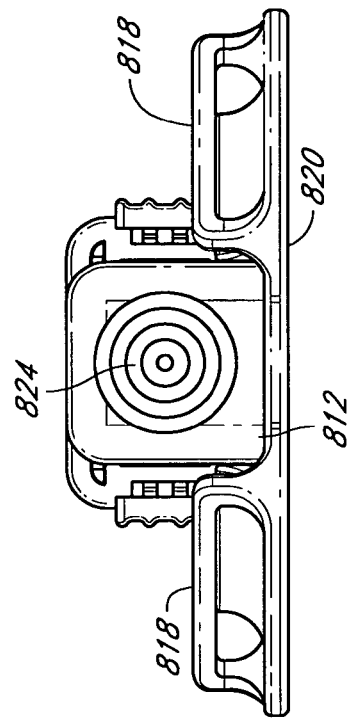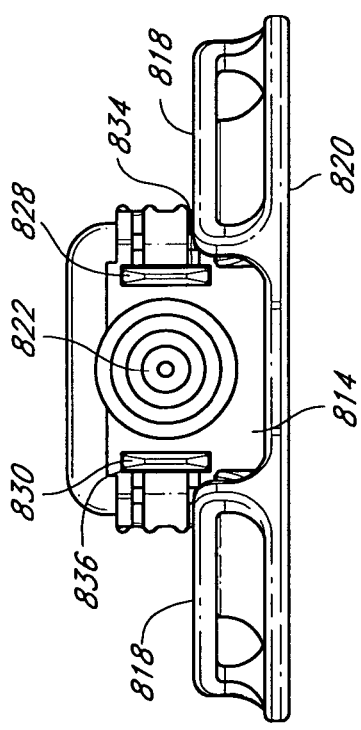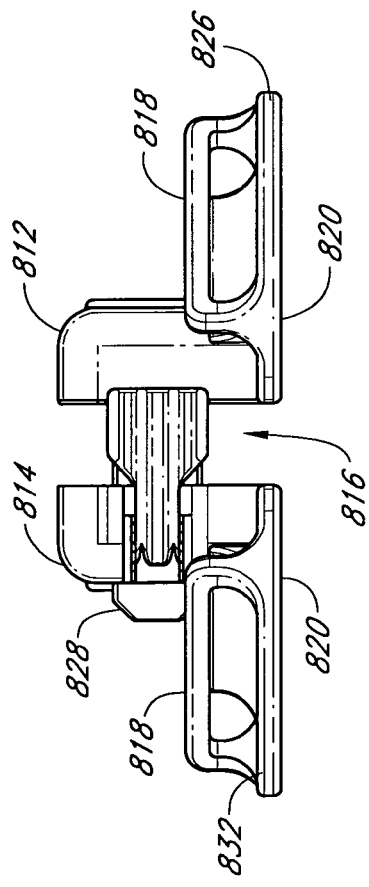

ENDO-TRACHEAL TUBE SECUREMENT SYSTEM

RELATED APPLICATIONS

This application claims the benefit of U.S. Provisional Patent No. 60/718,574, filed Sep. 19, 2005, and is a continuation-in-part of application Ser. No. 11/194,975, filed on Aug. 2, 2005, which is a continuation of application Ser. No. 10/826,689, filed on Apr. 16, 2004, now issued as U.S. Pat. No. 6,948,500 on Sep. 27, 2005, which is a continuation-in-part of application Ser. No. 10/270,883, filed on Oct. 11, 2002, now issued as U.S. Pat. No. 6,796,310 on Sep. 28, 2004, which claims the benefit of U.S. Provisional Application No. 60/328,727, filed on Oct. 11, 2001, each of which is hereby incorporated by reference in its entirety.

BACKGROUND OF THE INVENTION

1. Field of the Invention

This invention relates generally to techniques and systems for securing an endo-tracheal tube or other medical line to a patient. More specifically, this invention relates to an anchoring system and related techniques that maintain an endo-tracheal tube in position upon a patient and/or that prevent migration of the tube within the throat of the patient.

2. Description of the Related Art

When an endo-tracheal tube is used with a medical patient, it is common for the tube to be secured to the patient by means of adhesive tape. Failing to secure the endo-tracheal tube can result in the migration of the tube within the throat of the patient. Such motion is undesirable since outward motion of the tube can result in the tube moving entirely out of the airway of the patient, eliminating its effectiveness and potentially ventilating the patient's gastro-intestinal tract instead of the his lungs. Inward motion of the tube is undesirable because it will eventually result in the tube moving down one of the patient's bronchi, preventing air from being ventilated to the other lung. This will quickly lead to the collapse of the unventilated lung. Even slight back and forth motion of the tube within the throat can result in tracheomalacia and ultimately in the weakening or collapse of the trachea, which may require permanent stenting to maintain an open airway. Migration may further result in Ventilator-Associated Pneumonia (VAP). VAP is an airway infection that generally develops more than 48 hours after a patient has been intubated and has a high morbidity and mortality rate. VAP is a leading cause of death among patients with hospital-acquired infections, exceeding the rate of death due to central line infections, severe sepsis, and respiratory tract infections in the non-intubated patient and prolongs time spent on the ventilator.

In order to avoid these undesirable consequences, it is common to secure the endo-tracheal tube in the proper position upon the patient. For instance, a medical practitioner may, after positioning the tube properly within the throat of the patient, wrap adhesive tape around the tube and tape it to the patient. Various devices are often used as adaptors for endo-tracheal tubes, and sometimes these devices are taped to the patient. Other techniques can involve the use of straps which are wrapped around the head of the patient and which connect to the tube, or to the adaptor of the tube.

Such arrangements present certain problems for a medical practitioner. One difficulty is that once secured, it is generally not convenient to release or adjust the securement of the endo-tracheal tube. For instance, if an adhesive is used to secure the tube to the patient, adjusting or re-securing the tube in such situations requires that the adhesive be removed from the patient and the tube, and then fresh adhesive be used to properly re-secure the tube upon the patient. Such adhesive tape can be difficult to work with for medical practitioners wearing latex gloves, and contact with the adhesive can introduce tears or microscopic perforations into the gloves, compromising their effectiveness. Furthermore, repeated application and removal of adhesive from the face of a patient can irritate the skin of the patient.

Systems that use straps are often difficult to adjust and generally involve complex arrangements that can be difficult to position properly upon a patient. These systems can be difficult to remove from a patient as well. Furthermore, such systems for retaining an endo-tracheal tube in position often occlude the mouth of the patient. This can prevent a healthcare worker from having access to the mouth to allow for mouth care, such as suction of fluid from the oral cavity.

Therefore, a need continues to exist for an improved system to secure an endo-tracheal tube to a medical patient.

SUMMARY OF THE INVENTION

One aspect of the endo-tracheal tube securement system described herein includes a head contact member and at least four attachment members extending from the head contact member, a retainer having a posterior facing surface, a channel and a plurality of securing locations disposed on each side of the channel, the channel being configured to receive a portion of the endo-tracheal tube so as to inhibit movement of the endo-tracheal tube relative to the retainer, and the posterior facing surface being configured to inhibit movement of the retainer into the patient's mouth, and wherein the at least four attachment members are configured to attach to the plurality of securing locations so as to secure the endo-tracheal tube to the head contact member.

Another aspect is a securement system that includes a head contact member comprising a flexible strap in the form of a closed loop, the loop being sized to receive a portion of the skull of a patient such that the strap encircles at least the lambda of the skull, the loop being sufficiently small to prevent the skull from passing through the loop. The securement system further includes a plurality of securement straps attached to the head contact member and a retainer attached to the plurality of securement straps and configured to receive a portion of the medical article so as to inhibit movement of the medical article relative to the retainer.

Yet another aspect is a securement system including a retainer for retaining an endo-tracheal tube, the retainer having surfaces which contact skin proximate to a patient's mouth to inhibit movement of the retainer and endo-tracheal tube into the patient's mouth, the surfaces being disposed superior and inferior relative to the midline of the lips so as to allow access to the sides of the mouth, the retainer having attachment locations for attaching the retainer to securement members, at least one of the attachment locations being superior to the lips and at least another of the attachment locations inferior to the lips.

Another aspect is a method that comprises placing a head contact member on a patient's head, the head contact member being in contact with a plurality of securing straps and wrapping the plurality of securing straps around a portion of the patient's head, the plurality of straps being in contact with a retainer having a first portion and a second portion. The method further comprises generally aligning the first portion with the second portion on opposite sides of a medical tube and engaging the first portion with the second portion so as to inhibit movement of the medical tube relative to the retainer.

Another aspect is a method that comprises providing a plurality of securing straps, each having a first end portion and a second end portion, the first end portion contacting a head contact member and the second end portion contacting a retainer, wherein the retainer comprises a first portion and a second portion, contacting the head contact member to a patient's head, and wrapping the plurality of securing straps around at least a portion of the patient's head. The method further comprises generally aligning the first portion with the second portion on opposite sides of the medical tube and engaging the first portion to the second portion so as to inhibit movement of the medical tube relative to the retainer.

Another aspect is a method that comprises clamping an endo-tracheal tube between first and second portions of a retainer and using attachment locations superior to and inferior to the midline of the lips to secure the retainer to the patient's head.

Further aspects, features, and advantages of the present invention will become apparent from the detailed description of the preferred embodiments that follow.

BRIEF DESCRIPTION OF THE DRAWINGS

The invention will now be described with reference to the drawings summarized below. These drawings and the associated description are provided to illustrate a preferred embodiment of the invention, and not to limit the scope of the invention.

FIG. 9 illustrates the attachable fastener of FIG. 8 in use upon an endo-tracheal tube.

FIG. 10 illustrates a tube adaptor having eyelets in accordance with another preferred embodiment of the present invention.

FIG. 19 illustrates a top view of a retainer of the securement system of FIG. 16.

FIG. 20 illustrates a bottom view of the retainer of the securement system of FIG. 16.

FIG. 21 illustrates a side view of the retainer of FIG. 19 having a finger surface.

FIG. 22 illustrates an opposite side view of the retainer of FIG. 19 having a second finger surface.

FIG. 23 illustrates a side view of the retainer of FIG. 19.

FIG. 39 illustrates a side view of the retainer of FIG. 37 having a finger surface.

FIG. 40 illustrates an opposite side view of the retainer of FIG. 37 having a second finger surface.

FIG. 41 illustrates a side view of the retainer of FIG. 37.

DETAILED DESCRIPTION OF PREFERRED EMBODIMENTS

The following description and examples illustrate preferred embodiments of the present securement system disclosed in the context of use with an exemplary endo-tracheal tube. The principles of the present invention, however, are not limited to endo-tracheal tubes such as those shown. It will be understood by those of skill in the art in view of the present disclosure that the securement system described can be used with other types of medical articles, including, but not limited to: endo-tracheal tubes of different design, either with or without tube adaptors, naso-tracheal tubes, and the like. One skilled in the art may also find additional applications for the devices and systems disclosed herein. Thus, the illustration and description of the securement system in connection with an endo-tracheal tube is merely exemplary of one possible application of the securement system and technique disclosed.

Figure 1:
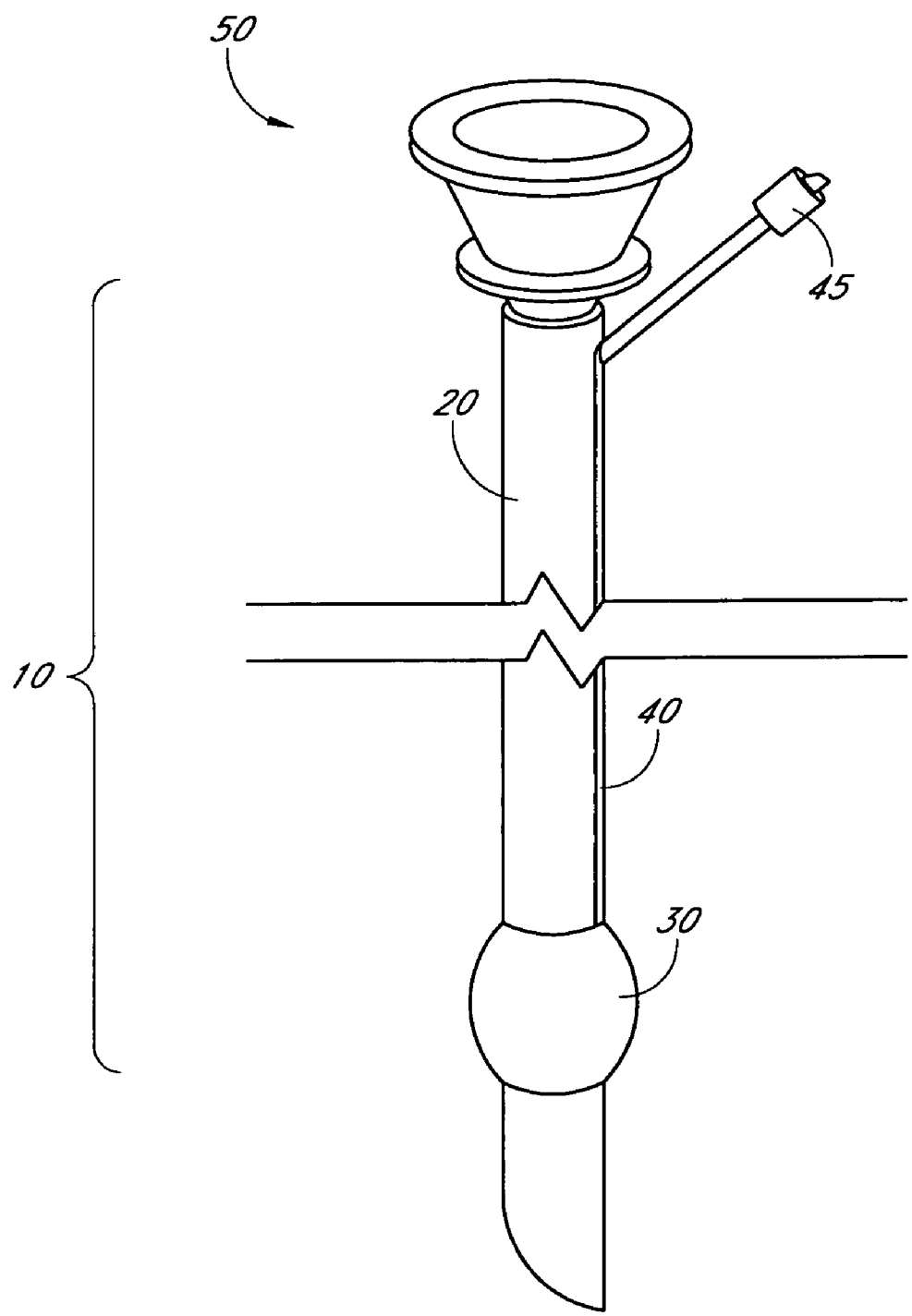
FIG. 1 illustrates an exemplary endo-tracheal tube and adaptor.

The exemplary endo-tracheal tube 10, as shown in FIG. 1, comprises an elongated tubular body 20 with a central lumen. The tube is inserted into the trachea of a medical patient, generally through the mouth. The endo-tracheal tube can include an inflatable balloon 30 located on the portion of the tube which is inserted into the throat. In order to provide the ability to inflate or deflate the balloon, a secondary inflation lumen 40 can extend from the balloon 30 portion of the tube along the tubular body 20 and can extend away from the tubular body at a location which will be located outside the patient at all times. A valve 45 is preferably disposed upon the end of this inflation lumen for use in controlling the inflation of the balloon.

As is shown, the endo-tracheal tube 10 can be used with an adaptor 50 which is disposed upon the external end of the endo-tracheal tube 10. This adaptor provides a connection between the lumen of the tube and any other tube or apparatus to which the endo-tracheal tube can be connected, such as a ventilator.

Overview

Figure 2:
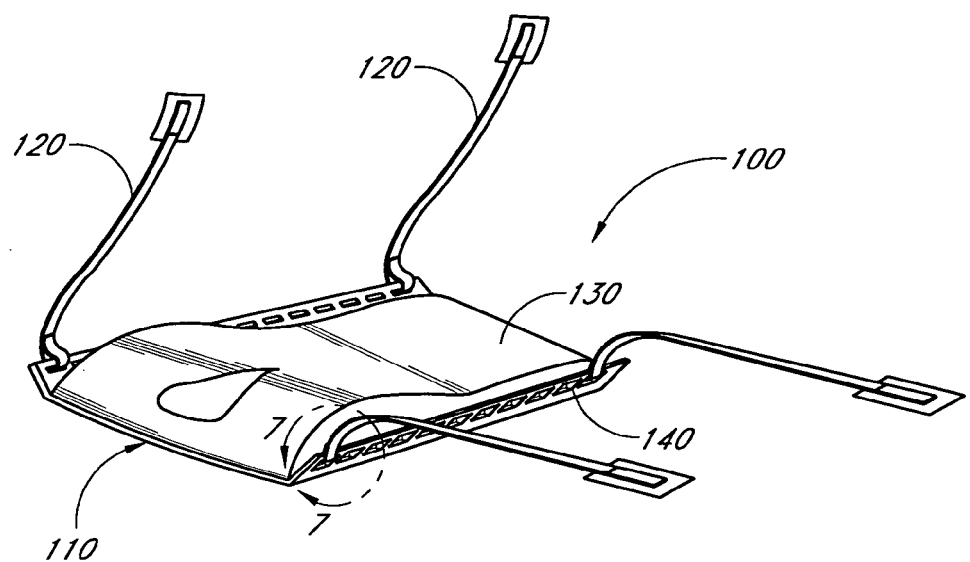
FIG. 2 illustrates one preferred embodiment of a securement system in accordance with the present invention.

As shown in FIG. 2, the securement system 100 described comprises a head pad 110 and one or more securing members 120. The head pad is designed to be placed underneath the head of the intubated patient. The head pad contains a head support 130 upon which the head and neck of the patient will rest. Disposed on each lateral side of the head pad are one or more slits 140 or holes through which one end of a securing member 120 can be inserted. In a preferred form, the head pad 110 includes a plurality of slits 140 and four securing members are attached to the head pad by inserting one end of each member through a slit upon the head pad, and then affixing them in position, for example via a hook and loop fastener arrangement (e.g., Velcro®) disposed upon the member. The free end of each securing member includes a mechanism to secure the member to the endo-tracheal tube or its adaptor. This can include an adhesive strip, a hook designed to attach to an eyelet upon the tube or adaptor, a clip component designed to engage a corresponding clip component (e.g., a receptacle) disposed on the endo-tracheal tube or adaptor, or such other fastener as is known to those of skill in the art. These will be discussed in greater detail below.

Once the patient is intubated and his head is placed upon the head pad 110, each of the four members 120 are attached to the tube 10 or tube adaptor 50. Once the members are attached, they are made snug by releasing their attachment to the head pad 110 and then re-securing the member 120 to the head pad after pulling the member taut. By this arrangement, a snug four-point securement can be made between the endo-tracheal tube 10 and the head pad 110, holding the tube in position upon the patient, and inhibiting undesirable migration of the tube within the throat of the patient. The system can easily be removed from the patient by releasing the members 120 from the head pad 110, allowing for quick release, as well as for readjustment of the positioning of the tube.

The above features will now be described in greater detail with reference to the included Figures.

Head Pad

Figure 3:
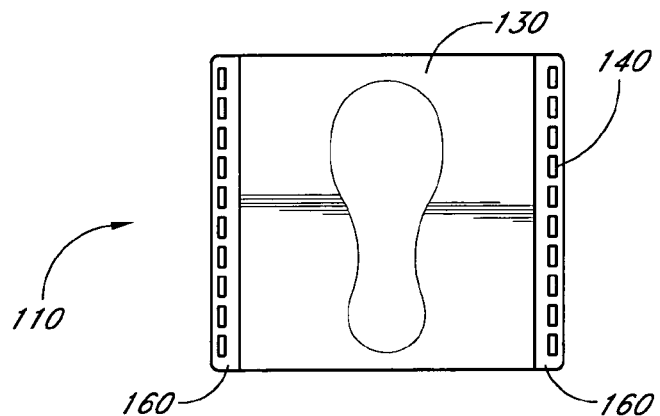
FIG. 3 illustrates a top view of the head pad of the securement system of FIG. 2.
Figure 4:
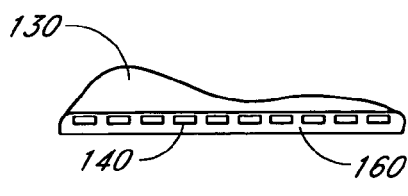
FIG. 4 illustrates a side view of the head pad of FIG. 3.
Figure 5:
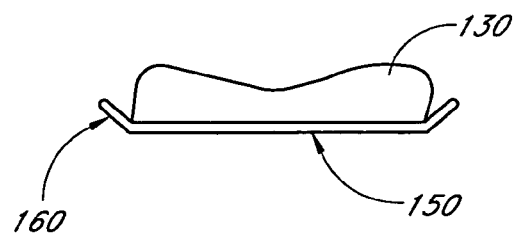
FIG. 5 illustrates a front view of the head pad of FIG. 3.
Figure 5A:
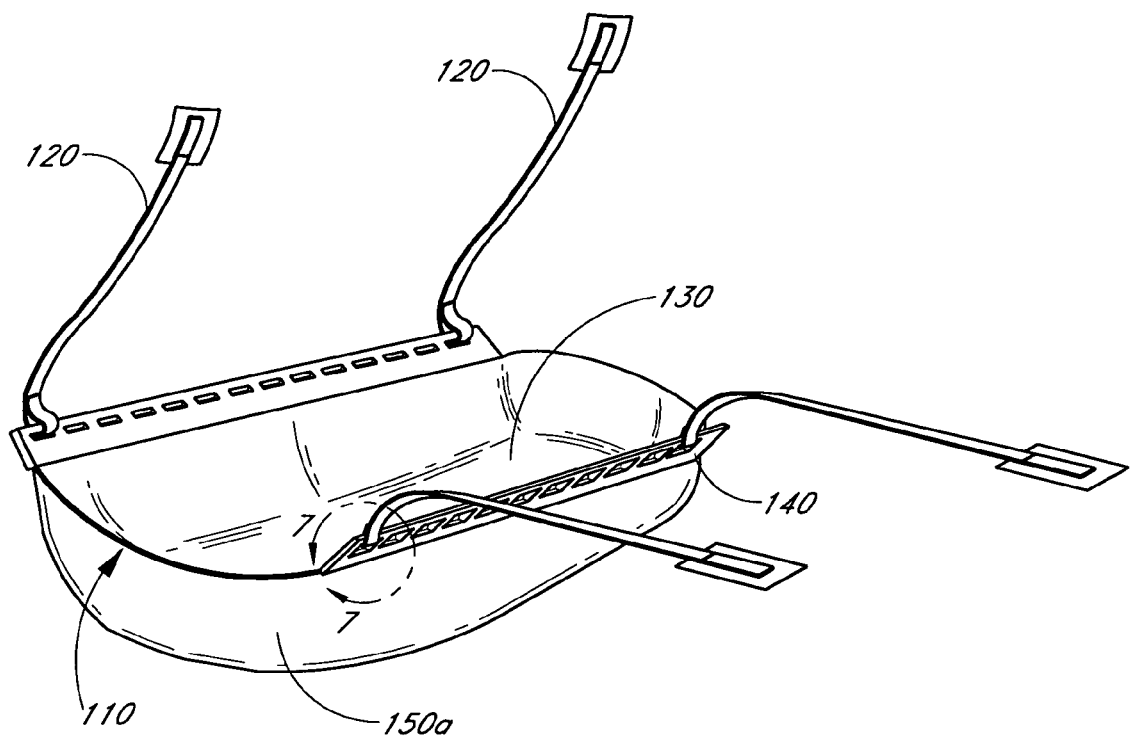
FIG. 5A illustrates a concave shaped head pad.

An exemplary head pad 110 for use in the described endo-tracheal tube securement system 100 is shown in FIGS. 3 to 5. FIG. 5A illustrates a concave shaped head pad 110. The head pad 110 comprises a concave base or platen 150, 150a. The head pad 110 may further include a head support 130 to provided cushioning to the patient. In the embodiments illustrated in FIGS. 3-5A, the head pad 110 comprises a concave base or platen 150, 150a and a head support 130. The head pad 110 illustrated in FIG. 5A comprises a curved or concave shaped base 150a. As illustrated by FIGS. 2 and 5A, the head pad 110 can have various shapes which allow the head pad to keep the members 120 taut between the back of the patient's head and the tube 10. The contact between the head pad and the patient's head region maintains tension in the members 120. The tension in the members 120 inhibits the tube 10 from undesirable migration within the throat of the patient.

The head pad 110 can have a shape which follows the natural contour of the patient's head or cranium. The head pad 110 illustrated in FIG. 5A has a generally concave shape that contacts the patient's head. While the illustrated head pad 110 in FIG. 5A has generally a truncated, cylindrical and concave shape, other shapes can be used. For example, the head pad can have a spherical, dome, or bowl shape which forms a cavity to receive the back of the patient's head. In such embodiments, the one or more slits 140 or holes may be arranged around the periphery of the head pad. As illustrated in FIG. 2, the head pad 110 can have a generally rectangular shape.

In the embodiment illustrated in FIGS. 3-5, the concave base or platen 150 is a generally rectangular plastic piece, which forms the lower body of the head pad 110 and which is bent upwardly along two opposite edges to form the securing regions 160 to which the securing members 120 will be attached. As shown in FIGS. 5 and 5A, the securing regions 160 extend both laterally and upwardly from the periphery of the concave base or platen 150, 150a. For the embodiment illustrated in FIG. 2, the concave base or platen 150 is generally sized such that the central rectangular portion of the head pad will extend both beyond the crown and chin of a patient, as well as to each side of the patient's head.

Each securing region 160 has a plurality of slits 140 or holes disposed along the longitudinal length of the securing region. Each hole is sized so as to accept one end of a securing member 120. As used herein, the word "end" is not intended to be limited to the actual terminus of a particular member. "End" is used broadly to refer to not only the terminus of a particular structural element, but also the region of the element which is near this terminus. While the concave base or platen 150, 150a can include as few as two slits on each securing region (for a total of four slits), it is more desirable that a larger number of slits be provided upon each securing region so that there are multiple positions in which each securing member can be attached. Each of the head pads 110 shown in FIGS. 2 and 5A includes ten slits in each securing region, although those of skill in the art will understand that the number of slits 140 can be varied without changing the nature of the invention.

By providing a greater number of positions to which the members 120 can be attached to the concave base or platen 150, 150a, the system can accommodate a greater variety of sizes of patient's heads with the same head pad 110. This also allows a particular member to be moved from one slit 140 to another in order to more effectively secure a medical device in position upon a patient.

The head support 130 is disposed on top of a portion of the concave base or platen 150, 150a. The head support forms a contoured surface that will support the head of the patient upon whom the endo-tracheal tube is being secured. The head support 130 is desirably somewhat pliant, so as to provide some cushioning to the head of the patient. The head support 130 can comprise a generally rectangular foam body when seen from above (see FIG. 3), with a generally flat bottom surface. The head support is generally dimensioned so as to fit upon a region of the concave base or platen 150, 150a, but not to extend onto the securing regions 160.

The thickness of the head support 130 can vary, and in particular can be contoured so as to provide effective support for the head and neck of a medical patient with the back of the head upon the head support and facing upwardly away from the platen 150. This can be accomplished by contouring the head pad 130 such that the region of the support located under the neck of the patient is thicker than the region under the head. In addition, the central region of the pad can be thinner than the sides so as to provide some lateral support for the head of the patient and to prevent the head from rolling to either side and possibly dislodging the endo-tracheal tube from its proper position. In addition, the thicker neck support region also prevents the head from rocking forward with the chin moving toward the chest. This motion can cause undesirable compression of the cervical vertebrae, as well as resulting in crimping or undesirable motion of the endo-tracheal tube within the throat of the patient.

The concave base or platen 150, 150a can be formed by injection molding from plastic or another suitable material. The head support 130 can be formed from foam or some other pliant material. The head support 130 can be attached to the concave base or platen 150, 150a by a layer of adhesive disposed upon the upper surface of the platen. The bottom surface of the head support can then be placed upon this adhesive to secure the pad in position upon the concave base or platen 150, 150a.

The head support 130 and the concave base or platen 150, 150a can both be formed in the successive stages of the molding process and secured via adhesive, or they can be manufactured separately and assembled afterward. In addition, it can be desirable in certain applications for the head pad 110 to be disposable, in which case, materials of lesser durability can be used for the concave base or platen 150, 150a and head support 130.

Securing Members

Figure 6:
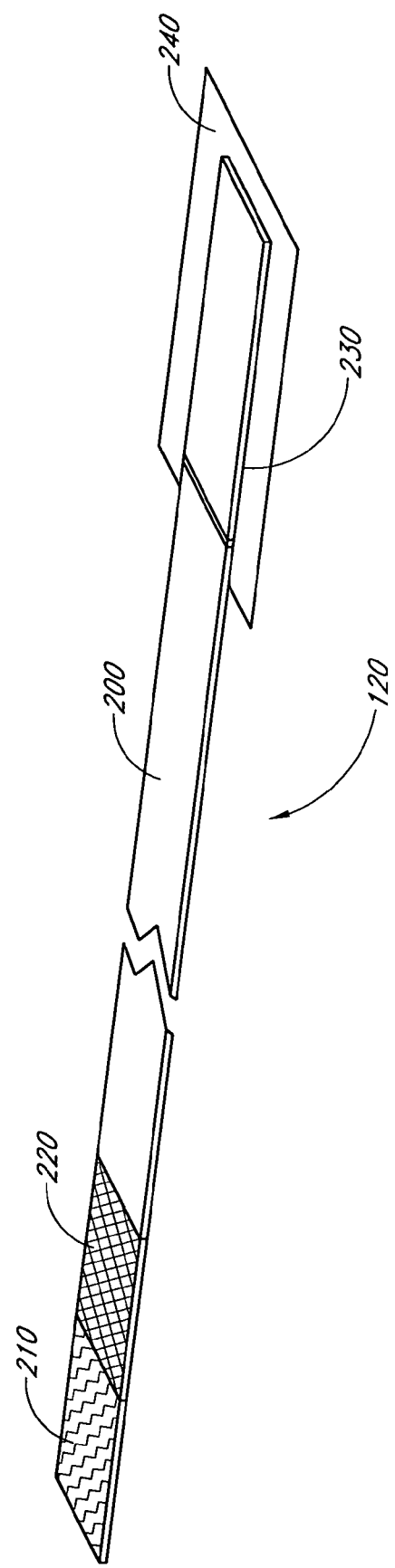
FIG. 6 illustrates a securing member of the securement system of FIG. 2.

As shown in FIG. 6, one preferred securing member 120 for use with the head pad 110 described above comprises an elongated flexible strip 200 of material which resists tearing. A variety of textiles can be used, such as a woven cotton-based textile. Woven plastic can also form a suitable material for the securing member. The member 120 is desirably long enough at least to reach from the edge of the head pad to about the mouth of the patient. The member 120 should also have enough additional length to allow it to be adjusted as necessary, as will be discussed below. This length can desirably be between about 10 and 20 inches in total length, depending upon the application.

One end of the securing member is desirably formed with hook and loop fastener material (e.g., Velcro®) disposed along one surface of the member. This can be seen in FIG. 6. For example, the end of the member can have the hook portion 210 of the fastener disposed upon the last portion of one surface, with the loop portion 220 disposed upon the adjacent portion of the same surface. The total size of the portion covered with hook and loop material can desirably be between 3 and 6 inches.

Figure 7:
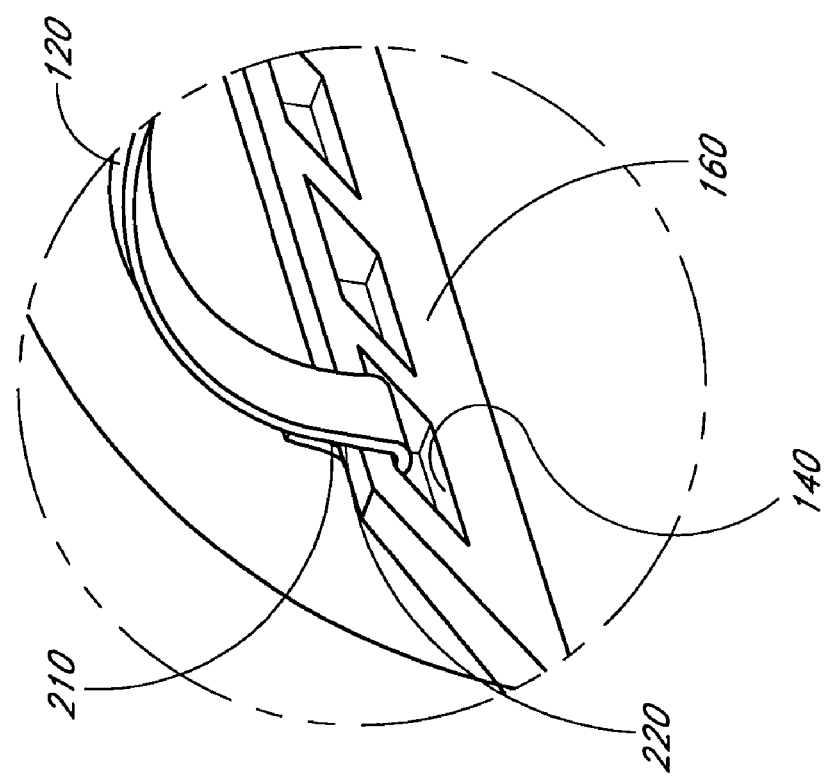
FIG. 7 is an enlarged view of the indicated portion of FIG. 2.

This end of the member 120 is used to attach the securing member to the head pad 110. The end of the member 120 with the hook and loop fastener is inserted through one of the slits 140 or holes of the securing region 160 of the head pad 110. Once inserted through, the member is folded around the edge of the securing region such that the hook portion 210 of the fastener is placed into contact with the loop portion 220 of the fastener on the end of the member. When the hooks and loops engage each other, the member 120 is now secured to the edge of the head pad 110, as shown in FIG. 7, which is an enlarged view of the circled region of FIG. 2.

The length of the free end of the member 120 can be adjusted by altering the location along the length of the hook and loop fastener at which the member wraps around the edge of the securing region 160 of the head pad 110. By pulling the hook and loop portions apart from one another, the member 120 is free to be slid through the slit of the head pad 110. Once it is pulled to the desired position, the hook portion 210 and loop portion 220 are brought together again and the member is now secured in the new position upon the head pad 110.

In order to provide a greater degree of adjustment of the overall free length of the member 120 which extends away from the slit 140 of the head pad 110, the length of the loop portion 220 of the hook and loop fastener can be extended along the member 120 away from the end with the hook portion 210. This provides a greater range of positions along the length along the member 120 to which the hook portion 210 can be secured via the loop portion 220. In particular, with a greater length of the member 120 over which the loop portion 220 extends, the member can be adjusted into a shorter overall length by securing the hook portion 210 to the loop portion 220.

The end of the member 120 without the hook and loop fastener includes a layer of adhesive 230 disposed on one side of the member. The portion of the member which has the adhesive coating is desirably between 1 and 4 inches long. This portion of the member is initially covered with a release layer 240. The release layer can comprise a paper or plastic layer which is placed over the adhesive region 230 to prevent inadvertent contact with the adhesive prior to attachment of the member 120 to the endo-tracheal tube 10 or adaptor 50.

Prior to use, the release layer 240 is peeled off of the end of the member, and the adhesive region 230 of the member 120 can then be wrapped around the endo-tracheal tube 10, or otherwise placed in contact with the tube 10 or its adaptor 50 in order to attach the tube or adaptor to the securing member 120. This process can be performed for as many or few of the members as is necessary to properly secure the tube.

Once each desired member 120 is secured to the tube 10 or adaptor 50, each member can be made snug by releasing member 120 from the head pad 110 where it is secured by the hook and loop fastener. The member can then be pulled taut to properly restrain the tub 10 in its position upon the patient.

Once taut, the hook and loop fastener can be used as described above to secure the member 120 at its new length to hold this taut position.

Attachable Fasteners

A variation upon the system described above for securing endo-tracheal tubes to a medical patient replaces the adhesive region 230 at the end of the member 120 with a different structure for fastening or connecting the end of the member to the endo-tracheal tube 10 or its adaptor 50. One such system uses a hook and an eyelet. In order to use such a system, appropriate eyelets or other rings, receptacles or apertures can be disposed upon the tube 10 or adaptor 50. Additionally, in some applications, it can be desirable to create apertures which are formed through the wall of the endo-tracheal tube and to which the members can be attached.

One technique for accomplishing this is to manufacture endo-tracheal tubes that have eyelets already molded on the tube. The eyelets are preferably located such that they are disposed at a location convenient for one or more of the members 120 to be attached to them. Another technique is to provide a separate set of attachable eyelets that can be quickly attached to a tube or adaptor when they are needed.

Figure 8:
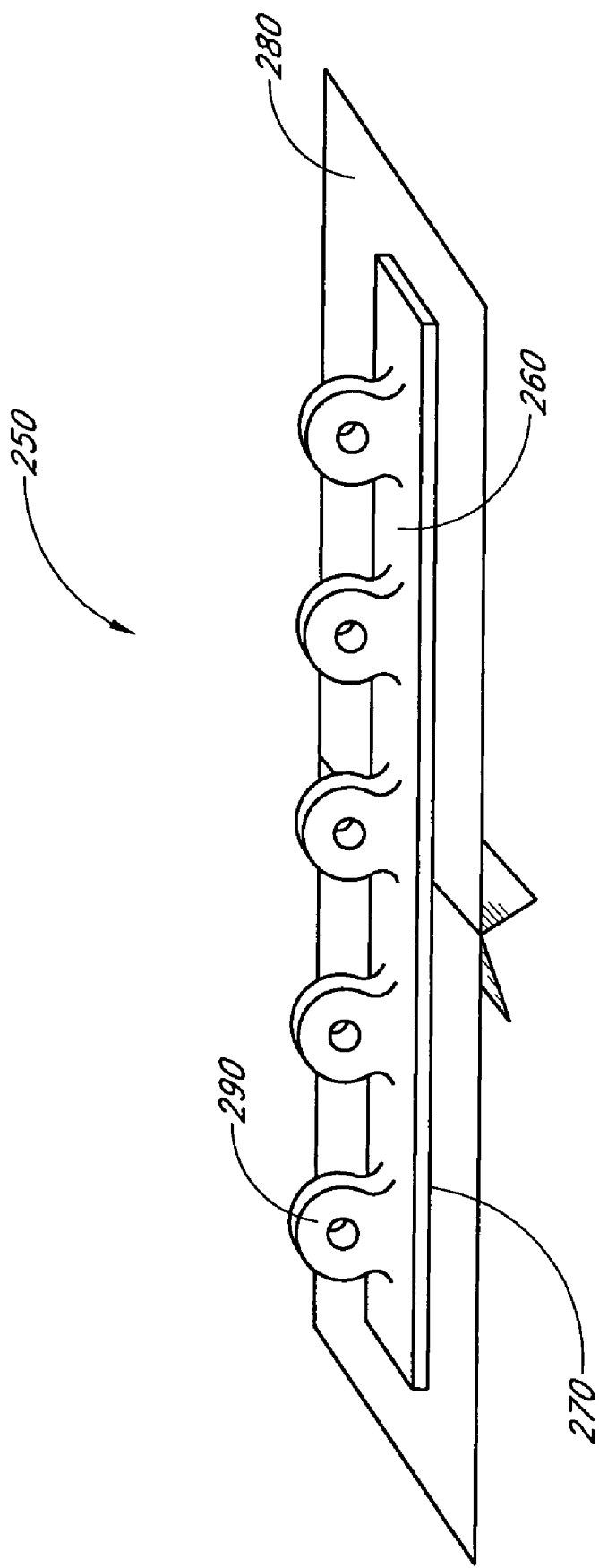
FIG. 8 illustrates an attachable fastener in accordance with another preferred embodiment of the present invention.

One set of attachable eyelets 250 for use with the present securement system is shown in FIG. 8. As can be seen, the attachable component comprises an elongated plastic or woven strip 260. One side of the strip is covered with an adhesive layer 270, and the adhesive layer is covered with a release liner 280 until it is ready for use in order to prevent unintentional adhesion. If desired, the release liner 280 can be split so that it can be peeled off in two sections, as shown in FIG. 8. The opposite side of the strip 260 includes a number of plastic or woven rings or eyelets 290 through which hooks from the securing members 120 can be inserted (described below).

The strip 250 shown in FIG. 8 shows the eyelets 290 arranged such that the axis of the opening of the eyelet 290 is normal to the long axis of the strip 260. However, those of skill in the art will recognize that the axis of the openings in the eyelets 290 need not be oriented in this direction. The eyelets 290 could also be oriented perpendicular to the arrangement shown so that the axis of all the eyelets was substantially aligned and was parallel to the long axis of the strip 260. Those of skill in the art will recognize that various angled arrangements for the eyelets are also possible, and that the axis of each eyelet need not be oriented in the same direction.

In order to use the eyelet strip 250, the adhesive layer 270 is exposed by peeling the release layer 280 from the strip 260. Once this region is exposed, the adhesive layer 270 of the strip 120 is then wrapped around the endo tracheal tube 10. This results in the configuration shown in FIG. 9. Once the eyelet strip 250 is mounted upon the endo-tracheal tube 10, securing members 120 can be used to connect the eyelets 290 to the head pad 110 of the securement system.

Those of skill in the art will also recognize that the fastener disposed upon the attachable strip need not be eyelets designed for use with hooks. Other arrangements include but are not limited to: snaps, clips, or such other fasteners as are known to those of skill in the art.

In addition to the system described above, other designs for attachable fasteners are also possible. For instance, rather than having the fastener elements disposed upon a flat strip 260 which is then wrapped around the endo-tracheal tube, it is possible to have the attachable fastener pre-formed into a short cylindrical piece or ring. The fasteners can be disposed upon this cylinder so that they form a configuration similar to that of the attachable eyelet strip 250 once attached to a tube, as shown in FIG. 9. Desirably, the cylinder is slit along its length at a location about its circumference to allow the cylinder to be flexed into a less curved position and then placed into position around the tube.

This ring-style attachable fastener can be formed of a flexible material which tends to hold its shape, but which can be flexed or bent by a medical practitioner without fracturing. The desired shape for such a fastener is substantially similar to the shape of the strip-style attachable fastener shown in FIG. 9 once it has been attached to the tube. The cylinder is placed in the desired position longitudinally upon the tube, and then it is released and allowed to return toward its original shape. In returning to its original unflexed shape around the tube, the cylinder can grip the outer surface of the tube even without the use of adhesive. Such an arrangement can be advantageous in circumstances where it becomes desirable to reposition the fasteners upon the tube. In order to improve traction between the cylinder and the tube 10, the inner surface of the tube can be roughened, or otherwise treated with a high friction coating to provide a better grip between the tube and cylinder. This will help inhibit any undesired motion of the cylinder upon the tube 10 once the cylinder is in position.

Other variations of fasteners which can be attached or disposed upon the tube or adaptor include flexible clamps to clamp fasteners around the outer surface of the endo-tracheal tube. Those of skill in the art will recognize that there are a variety of techniques which are applicable for attaching fastening elements to the endo-tracheal tube.

Tube Adaptor

Another technique for providing appropriate fasteners for the securing members is to provide fasteners, connectors or other anchoring receptacles, such as holes or eyelets, upon the endo-tracheal tube adaptor. For example, as shown in FIG. 10, eyelets can be disposed upon the tube adaptor for use with hooks disposed upon the securing members. As shown in FIG. 10, the tube adaptor 300 comprises a generally tubular plastic piece with a generally tapering diameter to its inner lumen 310. One end of the adaptor 300 is provided with a tapered region 320 which can be inserted into the end of an endo-tracheal tube 10, while the other end can be connected to an external tube of some kind, for example, the end of a ventilator.

As shown in FIG. 10, the adaptor 300 also can include suitable anchors for attachment to the securing members 120 of the endo-tracheal securing system 100. A number of eyelets 330 are shown disposed around the circumference of the central portion of the tube adaptor 300. This region of the adaptor 300 is between the end 320 of the adaptor that is inserted into the endo-tracheal tube 10, and the end of the adaptor 300 that attaches to an external medical tube or device.

As can be seen in FIG. 10, the eyelets 330 can desirably be disposed such that each of the axes of the holes of the eyelets are roughly tangential to the circumference of the tube adaptor 300 at the point where the eyelet is attached to the adaptor. Those of skill in the art will recognize that these eyelets can also be disposed such that the axes of the eyelets are generally all parallel to the axis of the adaptor 300 itself. In general, the eyelets 330 can be disposed in any arrangement which is suitable for cooperating with the hooks of the securing members 120. For instance, any of the orientations discussed with respect to the attachable eyelet strip 250 above can also be used here.

The number of eyelets 330 or other fasteners disposed on the adaptor 300 can vary, but is preferably at least equal to the number of members 120 which will be fastened to the adaptor 300. As is discussed above with respect to the attachable eyelets, a variety of different fasteners can be disposed upon the adaptor other than eyelets without altering the nature of the system described.

Securing Members with Fasteners

Figure 11:
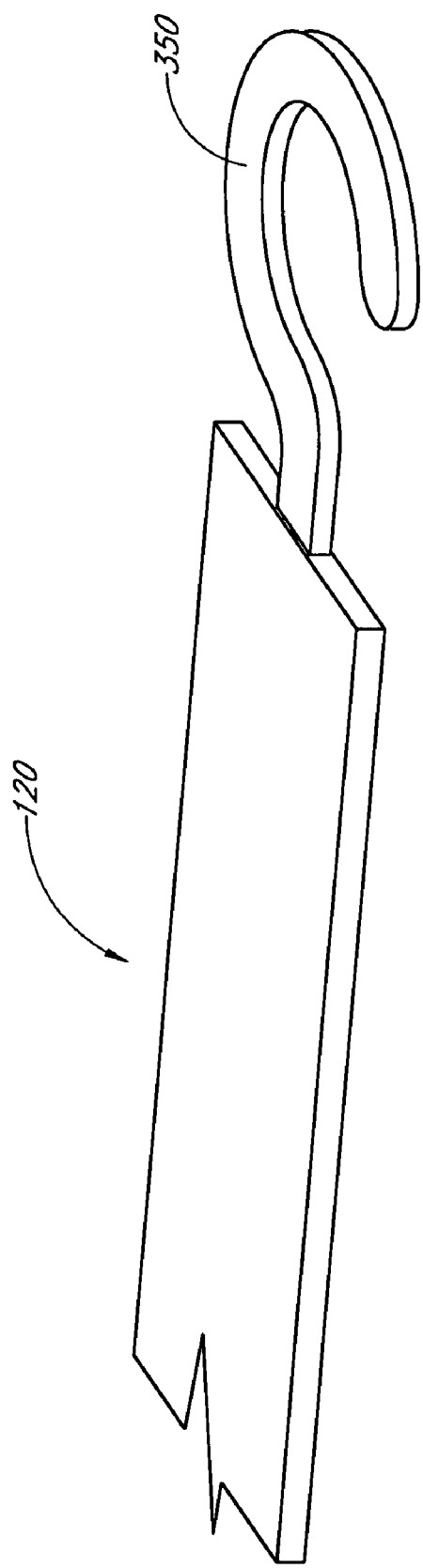
FIG. 11 illustrates a securing member in accordance with another preferred embodiment of the present invention.

In order to work with eyelets as shown with the attachable eyelet strip 250 or the tube adaptor 300 described above, a variation upon the securing members 120 described above can be used. One example of an appropriate member suitable for use with the eyelets 290, 330 described above is shown in FIG. 11.

The general structure and configuration of the securing member 120 is substantially the same as that shown in FIG. 6 and described above. The end of the member 120 which is attached to the head pad 110 is configured with hook and loop fasteners, and can be adjusted or released as described above. However, rather than an adhesive region upon the end of the securing member not attached to the head pad 110, a hook 350 is attached to the member 120. The hook 350 is dimensioned and configured to be inserted through an eyelet or other aperture disposed upon the tub 10 or adaptor 50, 300. These eyelets or apertures can be part of either an attachable eyelet strip 250 or a cylindrical ring with eyelets, as described above. The eyelets or apertures can also be integrally formed with the tube 10 or the tube adaptor 300.

When securing an endo-tracheal tube using the hooks 350 of these securing members in combination with either an attachable eyelet strip 250 or with an adaptor 300 having eyelets, the hooks 350 are placed through the eyelets 290, 330, and then the members 120 are made snug as described above by releasing the loop and hook fastener at the end of each member, pulling the member taut, and then re-securing the loop and hook fasteners to hold the member in this taut position.

Those of skill in the art will also recognize that if a fastener system other than a hook and eyelet combination is used that the hook can desirably be replaced by the appropriate portion of the fastener. For instance, if snaps are to be used, a snap receptacle can be disposed upon the securing member, and a snap protrusion can be disposed upon the attachable strip or adaptor.

Operation

Figure 12:
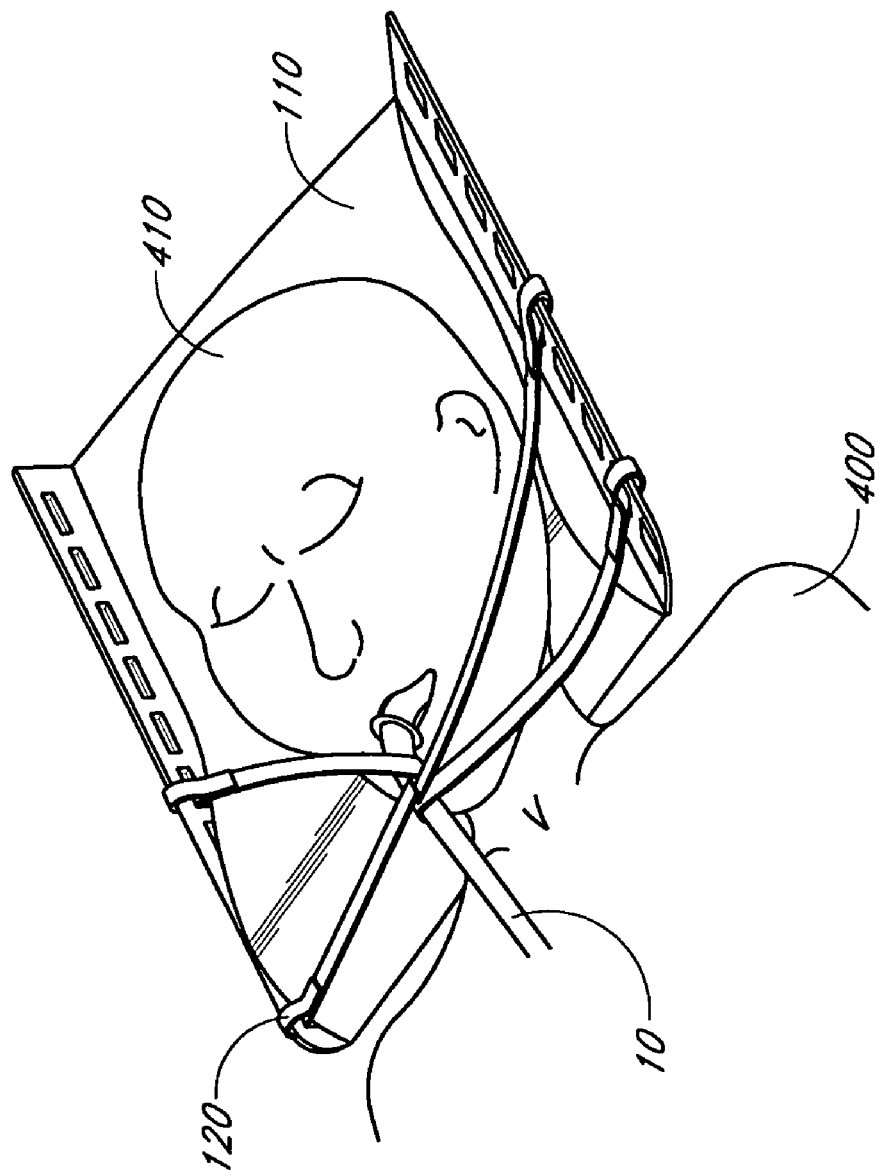
FIG. 12 illustrates the use of the securement system of FIG. 2 in use upon a patient.

As illustrated in FIG. 12, a medical attendant can secure an endo-tracheal tube 10 (or other medical article) to a patient 400 using the above-described securement system 100 (or a readily apparent modification thereof). The medical attendant places the head 410 of the patient 400 upon the head pad 110 such that the neck of the patient is properly supported by the head pad 110 and the head 410 is not rotated toward either side of the patient's body. This can be performed either before or after the patient is intubated.

If the securing members 120 are not already attached to the head pad 110, they can each be threaded through one of the slits 140 of the head pad 110, and then secured in position via the hook and loop fastener on each member 120. The securing members 120 can also be moved from one slit 140 to another in order to provide more appropriate anchoring points for the securement of the tube 10 upon the patient 400. For example, if the patient is young and has a smaller head, the position of the tube can be relatively closer to the end of the head pad than if the patient were fully grown. In order to accommodate this, it can be desirable to attach two of the members 120 to the head pad 110 at a position which is located partway down the length of the head pad, rather than closer to the end of the head pad. By providing multiple slits 140 on each side of the head pad 110, the system 100 can accommodate a wide variety of sizes of patients.

Once the members 120 are secured properly to the head pad 110, each member is attached to the endo-tracheal tube 10 or its adaptor. This can be accomplished via one of the techniques described above and will vary depending upon the type of fasteners provided upon the tube and members. For instance, if adhesive strips as shown in FIG. 6 are provided upon the securing members, the release liner 240 is removed and the adhesive is attached directly to the tube 10 or adaptor, as shown in FIG. 12.

If eyelets or snaps are disposed upon the tube or adaptor, then members with hooks or snap receptacles can be used to connect the members to the tube 10 or adaptor 50. In the case where no fastener is disposed upon the tube 10 or adaptor 50, an attachable fastener such as the attachable eyelet strip 250 described above can be attached to the tube 10 or adaptor as desired.

The connection between the head pad 110 and the tube 10 can be made secure by releasing the hook and loop side of each member 120 and pulling it snug between the head pad 110 and the tube 10. Once taut, the hook and loop fastener portions 210, 220 are re-secured. Once all the members 120 are snug, undesirable motion of the endo-tracheal tube 10 is inhibited.

Once secured in the above manner, the oral cavity of the patient 400 remains accessible to the medical practitioner. This allows for oral care such as suction to be performed without the need to remove the tube 10 from the patient 400, or to untape or otherwise undo the securement of the tube to the patient.

The described system allows a medical practitioner to adjust the position in which the tube 10 is secured if any adjustment becomes necessary. For example, if the tube's position must be adjusted upon the patient (e.g., if the patient has shifted, or it has been determined the tube is placed too deeply or too shallowly within the patient), this can be accomplished by the same procedure described above for making the members snug. The hook and loop fasteners of each member 120 are released, the tube 10 is repositioned, and then the members 120 are made snug and re-secured with the hook and loop fastener.

Similarly, if there is a need to rapidly remove the tube from a patient, the members 120 can be quickly released from the patient 400 by either removing the hooks or other fasteners from the eyelets, or in the case where an adhesive attachment is used between the members and the tube, the members 120 themselves can be quickly released from the head pad 110 by pulling the hook and loop fasteners open. This allows the members 120 to be removed from the head pad 110, and the entire tube 10 with the members still attached to be removed from the patient 400.

Variations

In addition to the variations described above, it is also possible to configure the system to use hook and eyelet pairs where the hooks are disposed not on the securing members, but on the medical articles to be secured instead. The appropriate eyelets can then be located on the free end of the securing members. In this way, the same securing operation as described above with respect to hook and eyelet fasteners can be used.

By placing the hooks in a fixed position upon the medical articles to be secured, such as the endo-tracheal tube or its adaptor, the free ends of the securing members need only include an eyelet or other aperture. This can simplify the manufacture of the members, and can also present certain safety advantages. Examples of such variations including these features are illustrated in FIGS. 13 to 15 and described below.

Figure 13:
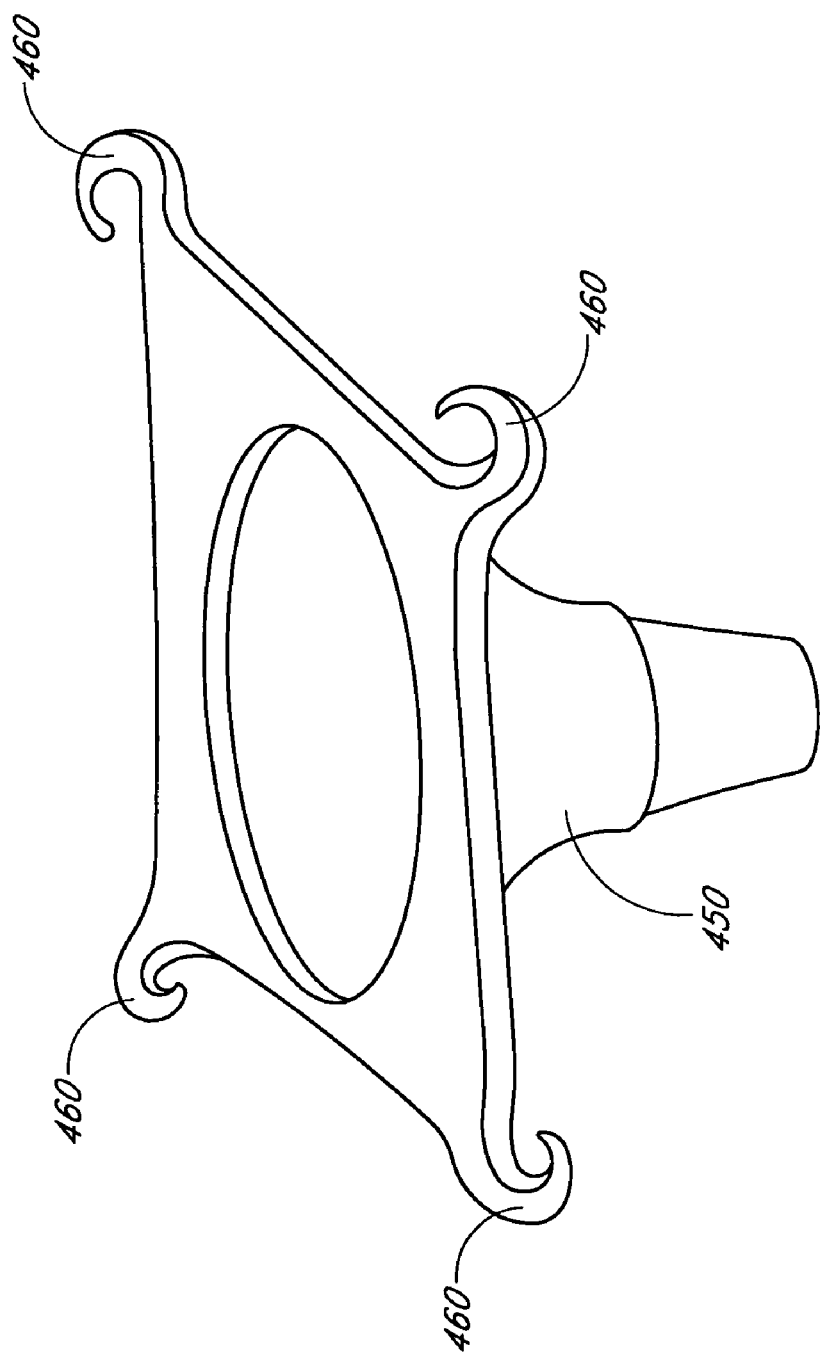
FIG. 13 illustrates a tube adaptor having hooks in accordance with another preferred embodiment of the present invention.

FIG. 13 illustrates an exemplary endo-tracheal tube adaptor 450 that includes hooks 460 suitable for use with securing members 120 that include eyelets or other apertures. If such an adaptor 450 is used with an endo-tracheal tube 10, the securing members 120 of the securing system can be attached to the hooks 460 on the adaptor 450.

Figure 14:
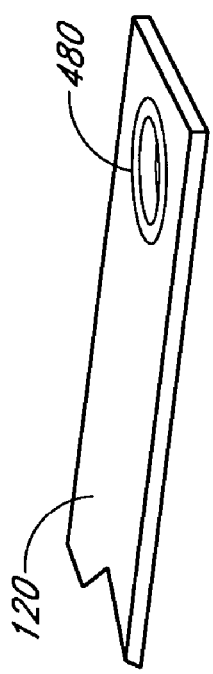
FIG. 14 illustrates a securing member for use with the adaptor of FIG. 13.
Figure 15:
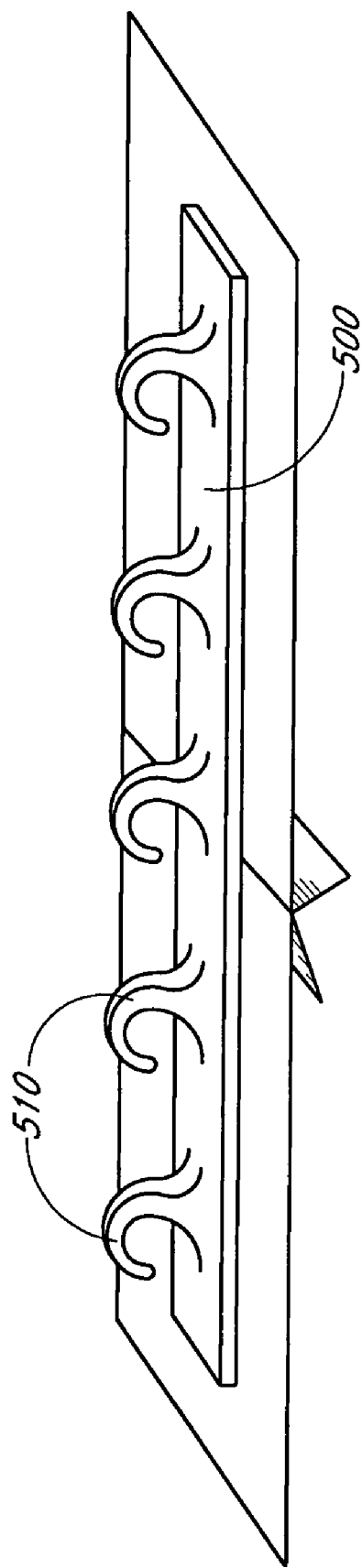
FIG. 15 illustrates an attachable fastener having hooks in accordance with another preferred embodiment of the present invention.

An appropriate securing member 120 for use with such hooks 460 is illustrated in FIG. 14. The free end of the securing member 120 is illustrated, and includes an opening 480, such as a hole or aperture, in the end of the member 120. The opening 480 is dimensioned to accept the hooks 460 on the adaptor 450 or other medical article to be secured. The opening on the member 120 can simply be a hole which is disposed near the end of the member, or can include a grommet or other support for the opening which helps inhibit any stretching or tearing of the member due to the pressure exerted between the hook 460 and the member 120.

Figure 14A:
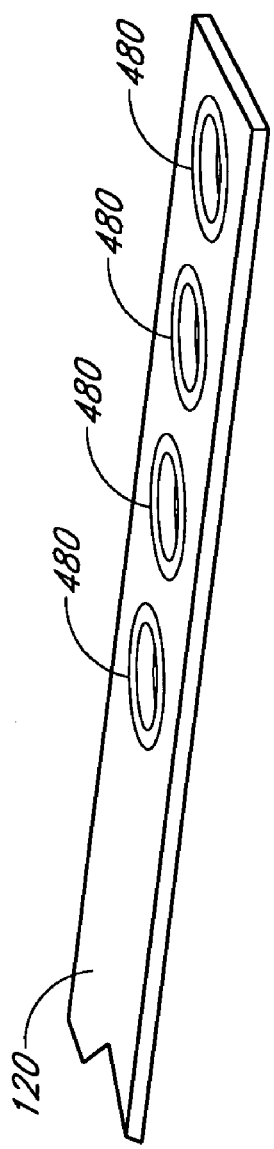
FIG. 14A illustrates another securing member suitable for use with the adaptor of FIG. 13.

As illustrated in FIG. 14A, the securing member 120 can also include a plurality of openings 480 in order to allow for simpler or more rapid adjustment of the connection between the head pad 110 and the medical article being secured. A member 120 including four openings is illustrated, but it will be understood by those of skill in the art that the number of openings 480 can be either greater or less than four without altering the nature of the system described.

Although the adaptor 450 shown in FIG. 13 has four hooks 460 disposed around the upper lip of the adaptor, the adaptor can also be configured with either a greater or lesser number of hooks. The position and direction of the hooks 460 can also be altered from that shown in the configuration of FIG. 13.

For instance, FIG. 13 shows the hooks 460 disposed radially about the upper surface of the adaptor. However, it is also possible to use an adaptor on which the hooks 460 are disposed from opposite sides of the upper surface of the adaptor, for example, two hooks extending from each of a pair of opposite lateral sides of the adaptor. Other possible arrangements include providing a greater number of hooks, for example six hooks disposed radially about the adaptor. Such an arrangement can be particularly well suited to adaptors which have a hexagonal upper lip. It is also possible to use an adaptor upon which the hooks are positioned at a location below the upper surface, similar to the position shown for the eyelets 330 in FIG. 10.

As described above with respect to the eyelet on the tube or adaptor, the individual hooks can be disposed such that the curved portion of the hooks extend in a plane normal to the axis of the tube, rather than extending in a plane parallel to the axis of the tube (as shown in FIG. 13).

In addition to the illustrated tube adaptor 450 with hooks 460 shown in FIG. 13, the securing members 120 of FIGS. 14 and 14A can also be used with an endo-tracheal or other tube which is integrally formed to include one or more hooks. These can be disposed in substantially the same positions and arrangements as the eyelets 290 are disposed upon the tube in FIG. 9. Similarly to what is described above, the hooks need not extend in a plane strictly normal to the axis of the tube, but can be disposed in a plane parallel to the axis of the tube.

For use with tubes 10 that do not have hooks molded upon them, an attachable fastener 500 with hooks 510 can be provided. Such an attachable fastener, as shown in FIG. 15, is substantially as described above with reference to FIG. 8. However, rather than including one or more eyelets disposed along the fastener, one or more hooks 510 are provided.

Although the attachable fastener 500 shown in FIG. 15 has hooks which extend along the length of the fastener, it will be understood that the hooks can extend across the width of the fastener without altering the nature of the system described.

Figure 16:
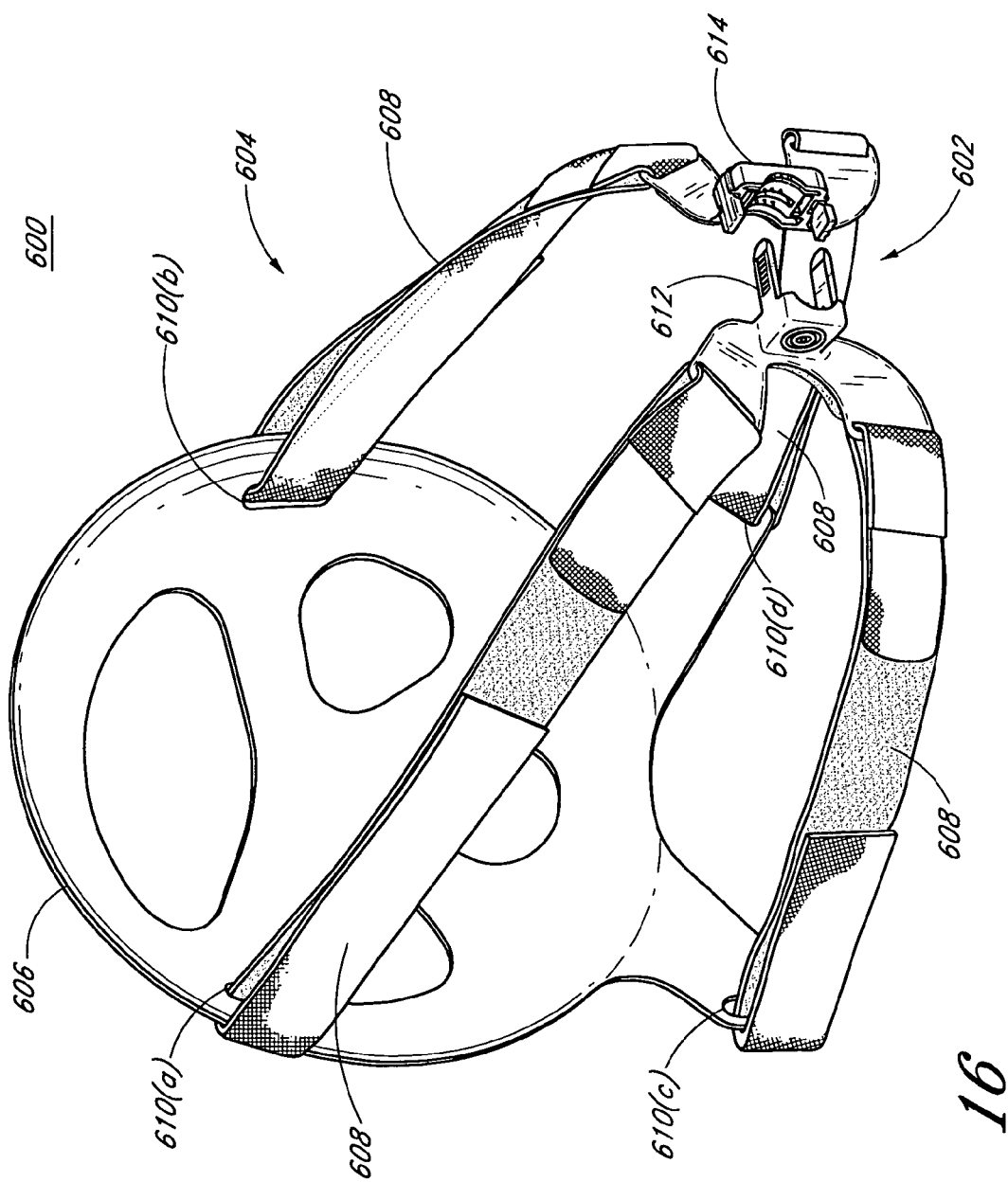
FIG. 16 illustrates another embodiment of a securement system in accordance with the present invention.

FIG. 16 illustrates another preferred embodiment of a securement system 600. The securement system 600 includes a retainer 602 which is secured upon the face of a patient by a harness 604. The harness 604 retains the retainer 602 in the operative position to support an endo-tracheal tube. The harness 604 which secures the retainer 602 to the patient's face includes a head contact member 606 and attachment members 608 for use in the described securement system 600. In the exemplary embodiment illustrated in FIG. 16, the head contact member 606 includes securing regions 610a, 610b, 610c, 610d extending from the head contact member 606. The securing regions 610a, 610b, 610c, 610d are spaced around the circumference of the head contact member 606 and form receiving slots for the attachment members 608. The securing regions 610 are configured to receive respective attachment members 608, and each includes at least one opening arranged so as to be accessible from a side of the head contact member 606.

Each attachment member 608 comprises a first end portion and a second end portion. In certain embodiments, the end portions each comprise hook and loop fasteners. The first end portion of the attachment member 608 is configured for attachment to the retainer 602. The second end portion of the attachment member 608 is configured for attachment to the securing regions 610 of the head contact member 606. For example, the openings in the securing regions 610 receive respective second ends of the attachment members 608 by passing each second end through an opening and then attaching the hook region of the hook and loop fastener to the loop region of such fastener. In certain embodiments, at least a portion of each attachment member 608 comprises a flexible elastic material. For example, the attachment member 608 may comprise VELSTRETCH made by Velcro USA Inc. located in New Hampshire.

The retainer 602 comprises a first portion 612 and a second portion 614. The first portion 612 is configured to engage with the second portion 614 forming a channel 616 therebetween (see FIG. 19). The channel 616 is configured to receive a portion of the endo-tracheal tube 10 and to retain the tube 10 so as to inhibit movement of the endo-tracheal tube 10 relative to the retainer 602 (see FIG. 30). In certain embodiments, the first retainer portion 612 releasably engages with the second retainer portion 614.

The retainer 602 includes a plurality of securing locations 618 located on the first and second portions 612, 614 (see FIG. 19). Each of the first and second portions 612, 614 comprises at least one securing location 618. In the embodiment illustrated in FIG. 19, each portion includes two securing locations 618. The securing locations 618 comprise openings configured to receive the first end portions of the attachment members 608. The width of the securing location 618 may be sized to accommodate the width of the attachment member 608. For example, the width of the attachment member 608 can be equal to or less than the width of the securing location 618 to facilitate threading of the ends of the members 608 through respective openings of the securing locations 618. In certain embodiments, the securing locations 618 are located superior and inferior to the lips of the patient when the retainer 602 is placed upon the patient's mouth.

The retainer 602 has a posterior facing surface which faces the patient and inhibits longitudinal movement of the retainer 602 into the patient's mouth. In certain embodiments, the posterior facing surface 620 contacts the patient superior and inferior relative to the midline of the lips and is configured to allow access to the sides of the mouth.

To enhance patient comfort, the posterior surface 620 may comprise a soft padding portion 621 of foam rubber or similar material. The padding portion 621 contacts the patient's face and bears upon the upper and lower lips to provide firm retainer support while cushioning the mouth and lips of the patient. The padding portion 621 is sufficiently soft and flexible to accomuodate variations between the profile of retainer 602 and the patient's face, thereby distributing contact forces and minimizing the trauma of extended periods of localized higher contact force.

While not illustrated, the first and second portions 612, 614 can include an adhesive and/or suture holes to secure the retainer 602 to the patient's face. For example, a hydrocolloid adhesive or zinc oxide-based adhesive can advantageously be used upon the posterior facing surface 620 for attaching the retainer 602 to the skin of the patient. The hydrocolloid or zinc oxide-based adhesive can be used either alone or in combination with another medical grade adhesive.

Figure 18:
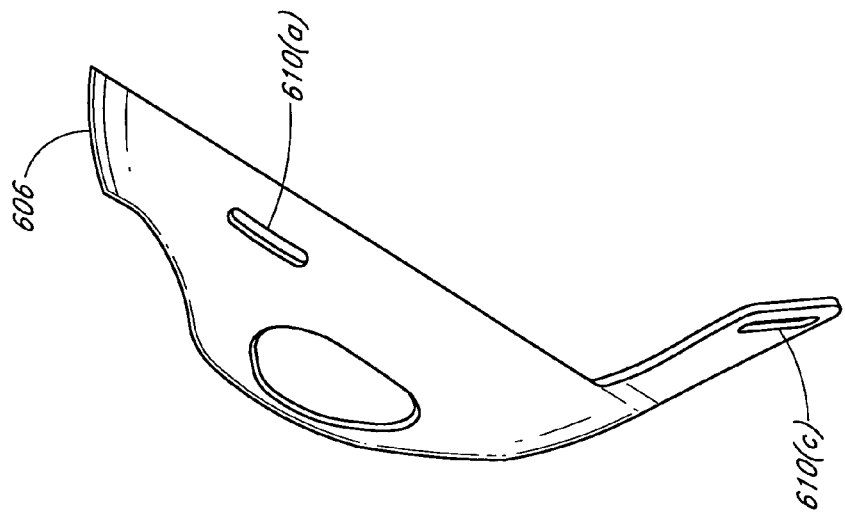
FIG. 18 illustrates a side view of the head contact member of FIG. 16.
Figure 17:
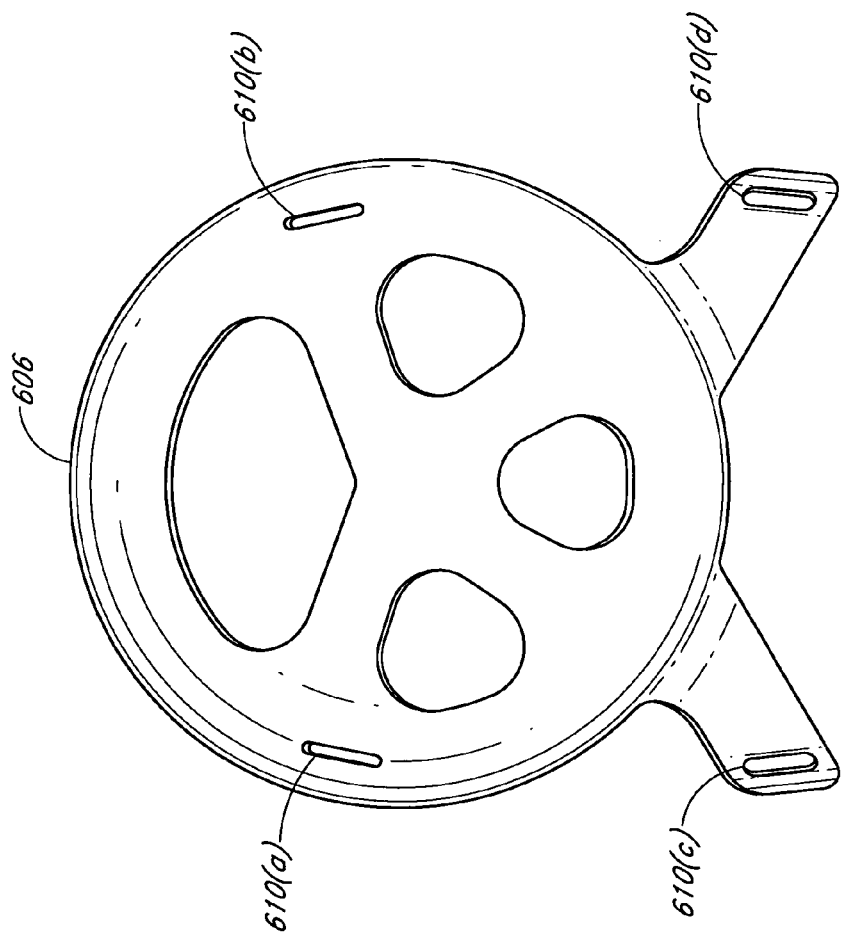
FIG. 17 illustrates a front view of a head contact member of the securement system of FIG. 16.

FIG. 17 illustrates a front view of the head contact member 606 of the securement system of FIG. 16, which shows the surface of the head contact member 606 that contacts the patient's skull. FIG. 18 illustrates a side view of the head contact member 606. The head contact member 606 comprises a curved or concave base. While the illustrated head contact member 606 has generally a concave shape, other shapes can be used. In certain embodiments, the head contact member 606 has a shape which follows at least a portion of the natural contour of the patient's skull. For example, the head contact member 606 can have a truncated cylindrical shape or a spherical, dome, or bowl shape which forms a cavity that matches the contour of the back of a human skull. In such embodiments, the securing regions 610 may be arranged around the periphery of the head contact member 606.

The head contact member 606 may further include a pad to provide cushioning to the patient. The pad can have various thicknesses which allow the head contact member 606 to keep the attachments members 608 taut between the back of the patient's head and the retainer 602. The attachment members 608 may include an elastic material which alone or in combination with the pad allows the head contact member 606 to keep the attachments members 608 taut between the back of the patient's head and the retainer 602. In use, the length of each attachment member 608 is adjusted to place them in tension. The contact between the head contact member 606 and the patient's head region maintains tension in the attachment members 608. The tension in the attachment members 608 coupled with the pressure of the posterior surface 620 against the patient's face inhibits movement of the retainer 602 relative to the patient, and thus, secures the retainer endo-tracheal tube 10 in position within the throat of the patient.

In the embodiment illustrated in FIGS. 17 and 18, the concave base, when viewed from the side (FIG. 18), is a generally hemispherical, single piece of plastic that includes the securing regions 610 to which the attachment members 608 may be attached. When viewed from the bottom (FIG. 17), the base has a generally circular central portion, with down and outward extending tabs of the head contact member 606 forming the securing regions 610c, 610d. For the embodiment illustrated in FIGS. 16 through 18, the head contact member 606 is generally sized such that the central portion, when positioned on the skull with the attachment members 608 in tension, places pressure on the occipital bone and preferably also on the parietal bone.

Each securing region 610a, 610b, 610c, 610d has a slit or hole. Each hole is sized so as to accept the second end portion of the attachment member 608. As used herein, the word "end" is not intended to be limited to the actual terminus of a particular member. "End" is used broadly to refer to not only the terminus of a particular structural element, but also the region of the element which is near this terminus. In certain embodiments, the securing regions 610 comprise a first plurality of securing regions 610a, 610c and a second plurality of securing regions 610b, 610d. In the illustrated embodiment, the first plurality of securing regions are disposed on a first side of the head contact member 606 and the second plurality of securing regions are disposed on a second side of the head contact member 606. While the head contact member 606 can include as few as two securing regions on each side (e.g., a total of four slits), more securing regions may be provided so that there are multiple positions in which each attachment member 608 can be attached. Those of skill in the art will understand that the number of slits can be varied without changing the nature of the invention.

The head contact member 606 may be sized for the patient's head. For example, an appropriately sized head contact member 606 may be selected based on the patient being an adult or child. By providing multiple sized head contact members 606, the system can accommodate a greater variety of sizes of patients' skulls while using the same attachment members 608.

The head contact member 606 of the disclosed embodiment forms a contoured surface that will support the head of the patient upon whom the endo-tracheal tube 10 is being secured. The head contact member 606 is desirably somewhat pliant, so as to provide some cushioning to the head of the patient. The head contact member 606 can be formed by injection molding from plastic or another suitable material.

FIG. 19 illustrates a top view (i.e., the side facing away from the patient) of a two piece retainer 602 of the securement system of FIG. 16. FIG. 20 illustrates a bottom view (i.e., the side facing towards the patient) of the retainer 602. The retainer 602 fastens or connects to the endo-tracheal tube 10. The securing locations 618 attach to the attachment members 608.

The retainer 602 shown in FIG. 19 shows the securing locations 618 arranged such that the plane of the opening of the securing locations is parallel to the posterior surface 620 of the retainer 602. However, those of skill in the art will recognize that the plane of the openings need not be oriented in this direction. The openings could also be inclined relative to the posterior or bottom surface. Those of skill in the art will also recognize that various angled arrangements for the securing locations 618 are also possible, and that the planes of the openings for the securing locations 618 need not be oriented in the same direction relative to the posterior surface 620.

In order to use the retainer 602, the first portion 612 and the second portion 614 are separated. Once separated, the first portion 612 and the second portion 614 are aligned with the endo-tracheal tube 10 therebetween (see FIG. 31 without the tube). The endo-tracheal tube 10 may first be placed, for example, within the groove or channel portion 616 formed by the first portion 612. The second portion 614 is then engaged with the first portion and completes the channel 616. The desired channel shape for such a retainer is substantially similar to the shape of the endo-tracheal tube 10.

Figure 30:
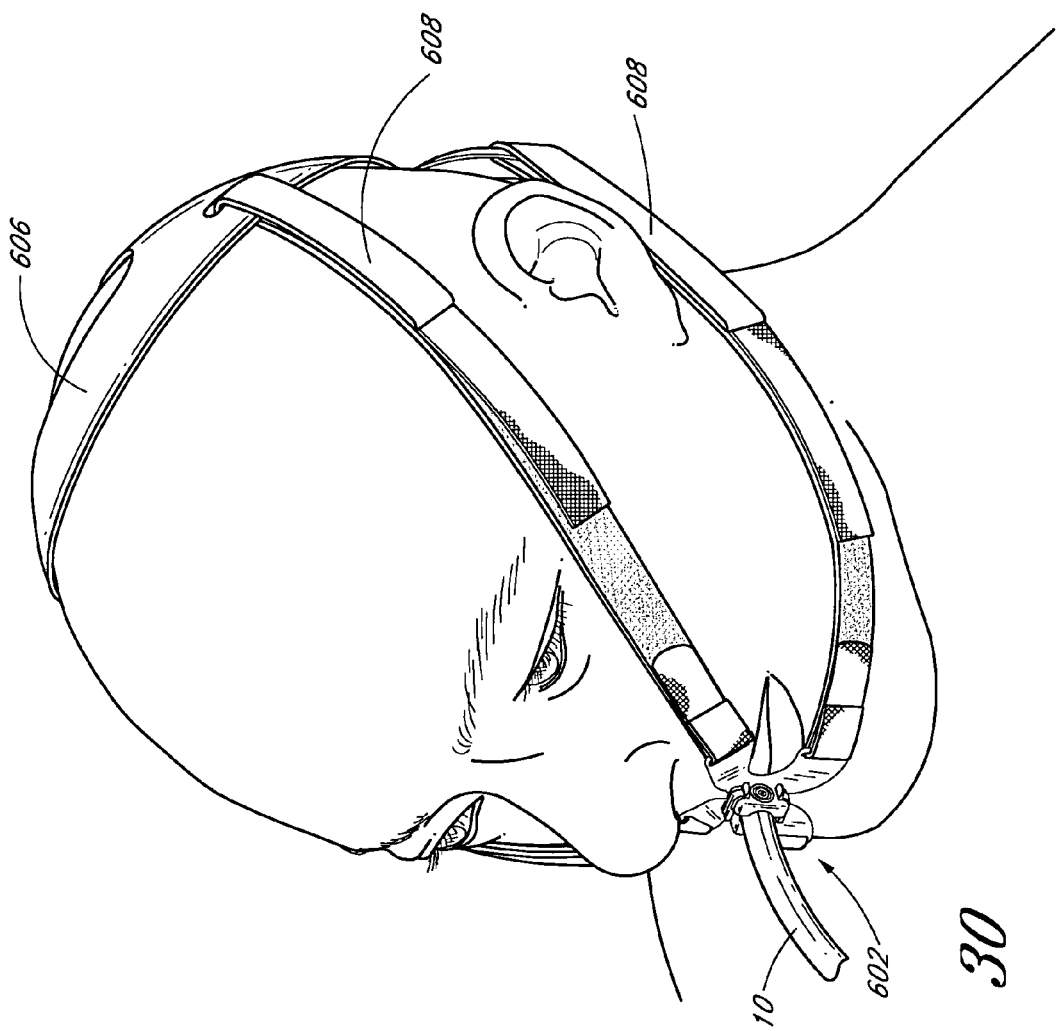
FIG. 30 illustrates the use of the securement system of FIG. 16 upon a patient.

With the first and second portions engaged, the retainer is disposed upon the endo-tracheal tube 10 and results in the configuration shown in FIG. 30. Once the retainer 602 is mounted upon the endo-tracheal tube 10 and the head contact member 606 is placed on the opposite side of the patient's skull, the attachment members 608 can be used to adjust the tension between the retainer 602 and the head contact member 606.

Those of skill in the art will also recognize that the openings of the securing locations 618 need not be designed for use with attachment members 608 in the form of straps. Other arrangements include but are not limited to: snaps, clips, or such other fasteners as are known to those of skill in the art.

The retainer 602 can be formed of a flexible material which tends to hold its shape, but which can be flexed or bent by a medical practitioner without fracturing. Suitable ridged but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 602 preferably is formed by injection molding using polyethylene or polypropylene material or nylon. However, other materials can be utilized, and the first and section portions of the retainer 602 may each be formed as a single piece.

FIG. 21 illustrates a side view of the retainer of FIG. 19 having a first finger pressure surface 622. FIG. 22 illustrates an opposite side view of the retainer of FIG. 19 having a second finger pressure surface 624. The first and second finger surfaces 622, 624 provide regions for a medical attendant to squeeze the first portion 612 and the second portion 614 together to form the retainer 602. The retainer 602 is first placed in the desired position longitudinally upon the endo-tracheal tube 10. The retainer is then squeezed around the endo-tracheal tube 10 so as to grip the outer surface of the endo-tracheal tube 10 even without the use of adhesive. Such an arrangement is advantageous in circumstances where it becomes desirable to reposition the retainer 602 upon the endo-tracheal tube 10.

In order to improve traction between the retainer 602 and the endo-tracheal tube 10, the outer surface of the endo-tracheal tube 10 can be roughened, or otherwise treated with a high friction coating to provide a better grip between the endo-tracheal tube 10 and retainer 602. This will help inhibit any undesired motion of the retainer 602 upon the endo-tracheal tube 10 once the retainer 602 is in position.

FIG. 23 illustrates a side view of the two-piece retainer of FIG. 19 with a first portion 612 engaged with a second portion 614. Each of the first and second portions 612, 614 is a one-piece molding of plastics material. Each portion 612, 614 includes a groove as described below. As best illustrated in FIGS. 21 through 23, the posterior surfaces 620 (facing the patient) are preferably contoured. The contour may be selected to follow the curvature of the patient's face. Advantageously, a contoured surface that follows the curves of the patient's face increases the contact area between the retainer 602 and the patient's face and evenly distributes the weight of the retainer 602 and any tension from the attachment members 608.

Figure 27:
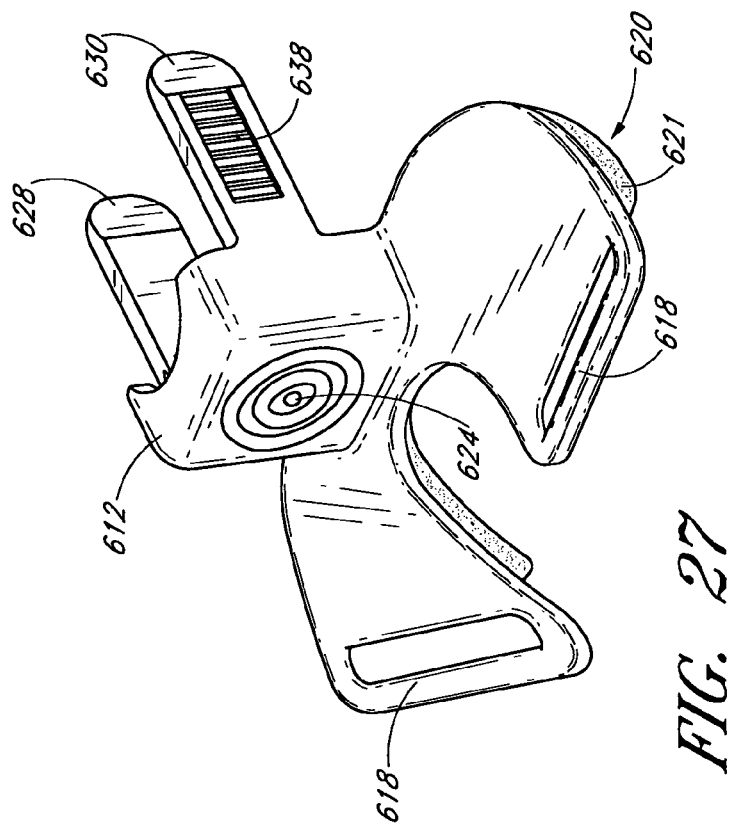
FIG. 27 illustrates an opposite side perspective view of the first portion of the retainer of FIG. 26.
Figure 26:
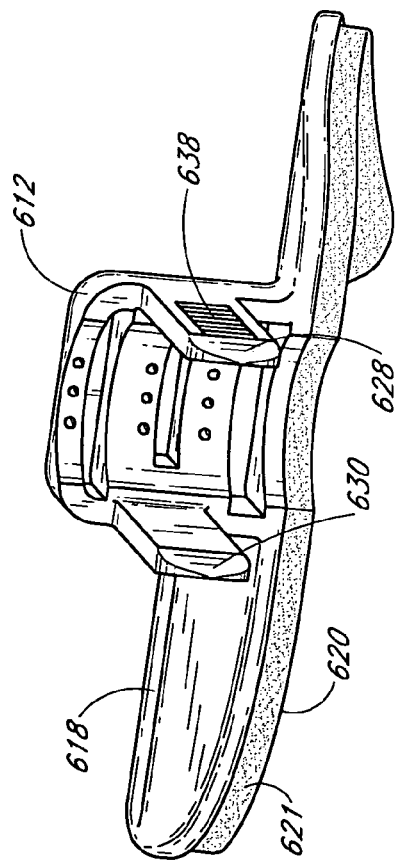
FIG. 26 illustrates a perspective view of a first portion of the retainer of FIG. 19.

FIGS. 26 and 27 illustrate perspective views of a first portion 612 of the retainer of FIG. 19. The first portion 612 comprises an anchor foot 626 (see FIG. 23), a pair of transversely extending parallel flexible prongs 628, 630, and the securing locations 618. The prongs 628, 630 are preferably integrally formed with the first portion 612. In FIGS. 19, 21, and 23, prongs 628, 630 are shown engaged with the second portion 614 to secure an endo-tracheal tube 10 in place.

Figure 29:
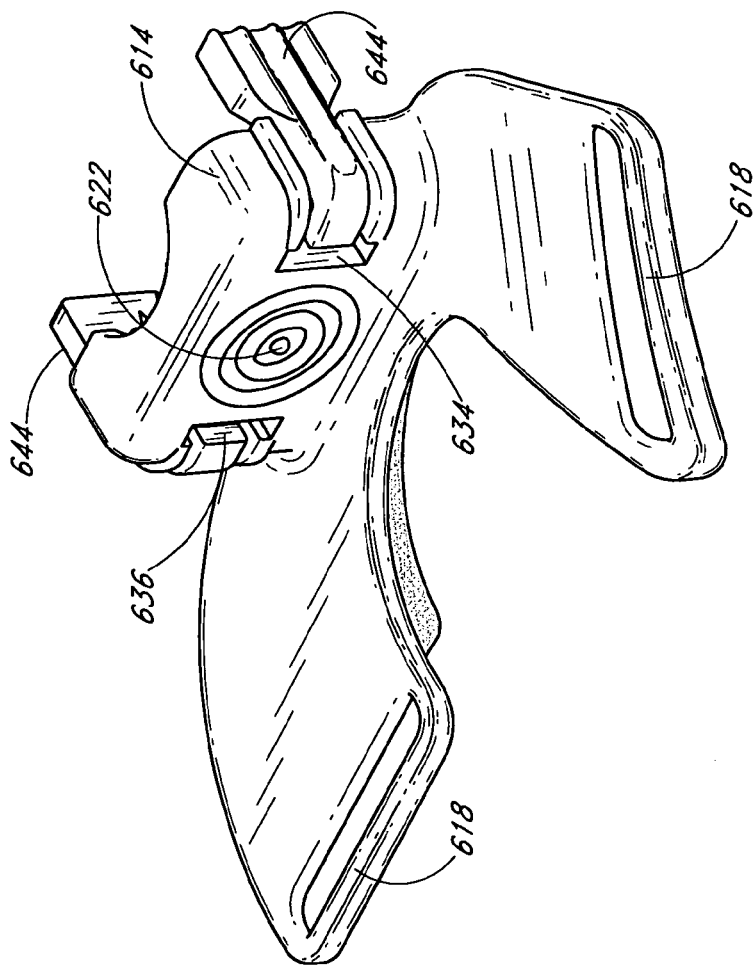
FIG. 29 illustrates an opposite side perspective view of the second portion of the retainer of FIG. 28.
Figure 28:
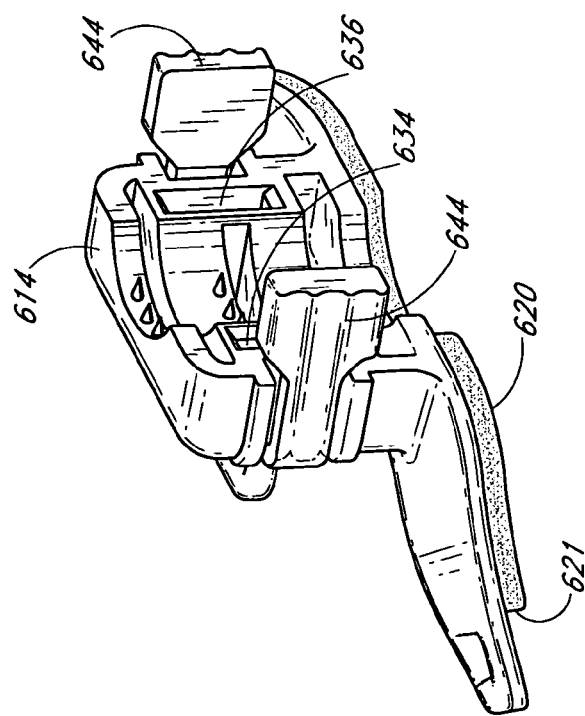
FIG. 28 illustrates a perspective view of a second portion of the retainer of FIG. 19.

FIGS. 28 and 29 illustrate perspective views of a second portion 614 of the retainer of FIG. 19. The second portion 614 comprises an anchor foot 632 (see FIG. 23), a pair of transversely extending parallel receptacles or apertures 634, 636, and securing locations 618. The receptacles 634, 636 are configured to receive the prongs 628, 630 of the first portion 612. In the illustrated embodiment, the anchor feet 626, 632 (see FIGS. 19 and 23) desirably include a pair of opposing concave sections that narrow the center of the anchor feet 626, 632 proximate to the center of the retainer 602. As a result, the narrow regions of the anchor feet 626, 632 provide clearance to access the sides of the patient's mouth for oral care and other nursing care as required. The wide regions of the anchor feet 626, 632 provide support and stability above and below the patient's mouth.

The two portions 612, 614 are adapted to be engaged, as shown in FIG. 19, so as to define a tubular channel 616 therebetween for receiving the endo-tracheal tube 10. The channel 616 is formed by respective generally hemispherical grooves in the first and second portions. Once engaged, the first and second portions are laterally slidable together so as to reduce the channel 616 cross-sectional area and firmly grip the endo-tracheal tube 10. The first and second portions are inhibited from sliding apart by interengaging structure as described below.

Figure 25:
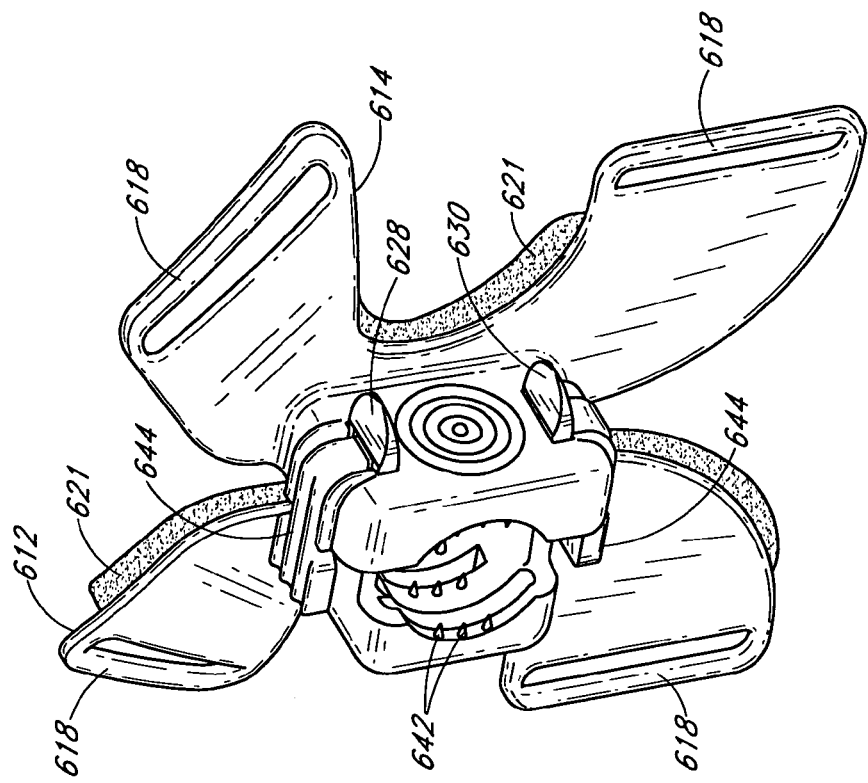
FIG. 25 illustrates an opposite side perspective view of the retainer of FIG. 19.
Figure 24:
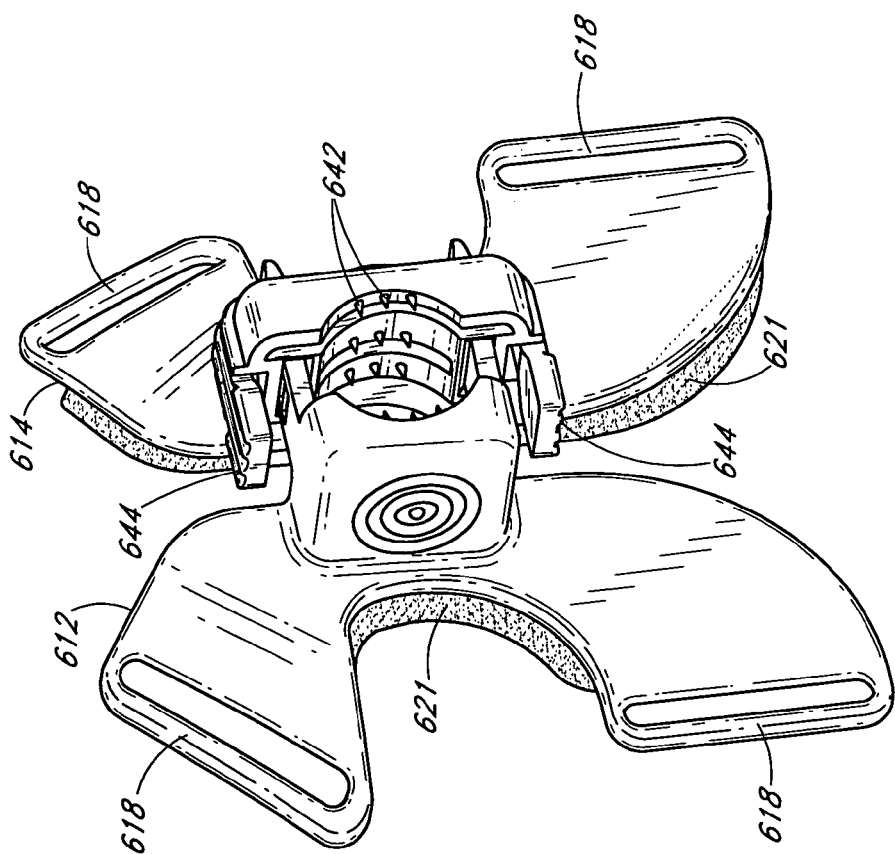
FIG. 24 illustrates a perspective view of the retainer of FIG. 19.

Each groove has a generally hemispherical cross-sectional shape. As best seen in FIGS. 24 and 25, the groove has a uniform width along the longitudinal axis. In certain embodiments, the groove varies in width (i.e., in the lateral direction) along its longitudinal length. That is, in certain embodiments, the side walls of the groove diverge from each other in, for example, a generally linear manner from one longitudinal side of the retainer 602 to the other longitudinal side of the retainer.

To firmly hold the endo-tracheal tube 10 within the channel 616, the retainer 602 includes interengaging structure. The interengaging structure inhibits the first portion 612 and second portion 614 from slidingly disengaging from one another. The interengaging structure may be releasable or not.

In the illustrated embodiment and as best seen in FIGS. 26-29, the interengaging structure is a releasable latch mechanism. The latch mechanism is used to secure the first portion 612 to the second portion 614. In the illustrated embodiment, the latch mechanism comprises interfitting teeth 638 (see FIGS. 26 and 27) provided on prongs 628, 630 and a pair of receptacles 634, 636 (see FIGS. 28 and 29) of complementary shape to the prongs. Each receptacle 634, 636 includes an inner edge which locks with the teeth 638 on the prong 628, 630. The inner edges of the receptacles 634, 636 snap against the teeth 638 when the prongs 628, 630 are inserted through the receptacles 634, 636 forming the closed position. In the illustrated embodiment, the latch mechanism is formed with the retainer 602 as a unitary piece.

In FIG. 21 the prongs 628, 630 are shown inserted through the receptacles 634, 636. The prongs 628, 630 interact with the receptacles 634, 636 formed in the second portion 614 to secure the prongs 628, 630 in their operative positions inhibiting the first portion 612 from moving away from the second portion 614.

FIGS. 24 and 25 illustrate perspective views of the retainer 602 of FIG. 19. As seen in FIG. 25, prongs 628, 630 have been inserted through receptacles 634, 636 and the prong teeth 638 engage with corresponding edges or teeth on the second portion 614 to clamp the endo-tracheal tube 10 in place within the channel 616.

The prong teeth 638 or serrations may be on both sides of the prongs 628, 630 to increase holding strength. In the illustrated embodiment, the teeth 638 are arranged on the side of the prongs 628, 630 facing away from the longitudinal axis while the inner edges of the receptacles 634, 636 are arranged on the sides of the receptacles facing the longitudinal axis;

however, these components can be flip-flopped. In a flip-flopped arrangement, outward pressure is applied to the prongs 628, 630 to disengage the teeth 638 from the edges in the receptacles 634, 636. Of course other interengaging structure known to one having ordinary skill in the art could be used. For example, Velcro, snaps, clips or the like could be employed to secure the first and second portions 612, 614.

An entrance of the receptacle 634, 636 may include chamfer edges. The chamfer edges slope inward toward the center of the receptacle to cause the teeth 638 to bend inward when inserting the prong into the receptacle.

In operation, the ends of the prongs 628, 630 bend toward the longitudinal axis of the retainer when inserted into the receptacles 634, 636. The relatively thin strip of material forming each prong 628, 630 allows the prong to bend when finger pressure is exerted on the finger surface 622, 624 (see FIGS. 27 and 29) to close the retainer. The interaction between the teeth 638 and the corresponding edge surface of the receptacle 634, 636 holds the prongs 628, 630 in the closed position and, once engaged, inhibits migration of the first portion 612 away from the second portion 614.

For embodiments having releasable interengaging structure, the structure is simply released to remove and replace an endo-tracheal tube 10 within the channel 616 of the retainer 602. In certain embodiments, a medical attendant presses downward on platforms 644 (see FIGS. 24 and 25) to disengage the prongs 628, 630 from the inner edges and slides the first portion 612 away from the second portion 614. The platforms 644 pivot towards the longitudinal axis and contact the outer surface of the prongs 628, 630. Further pressure on the platforms 644 deflects the prongs 628, 630 away from the edges of the receptacles 634, 636 and towards the longitudinal axis. As the prongs 628, 630 move towards the longitudinal axis, the teeth 638 disengage from the edges of the receptacles 634, 636 releasing the first portion 612 from the second portion 614. While maintaining pressure on the platforms 644, the medical attendant separates the first portion 612 from the second portion 614. The medical attendant can then open the retainer 602 and expose the channel 616.

The same retainer 602 may be used multiple times, so as to permit repeated attachment and reattachment of the endo-tracheal tube 10 to the securement system 600. In addition, the medical attendant can use the retainer 602 with any of a wide variety of size tubes. In addition, the latch mechanism being integral with the retainer 602 ensures that the latch mechanism will not be lost or misplaced if the endo-tracheal tube 10 is detached from the securement system 600.

The grooves formed in the first and second portions 612, 614 define the channel 616 when the retainer 602 is in a closed position. The channel 616 is capable of receiving a portion or length of the endo-tracheal tube 10 and is generally configured to house, grip and secure the affected endo-tracheal tube 10 in a contact area of the channel 616. The channel 616 can have a variety of configurations, as discussed above in connection with the grooves in order to accommodate a particular tube. As the interengaging structure provides multiple positions, and thus multiple channel widths, to lock the first portion 612 to the second portion 614, a single retainer 602 may accommodate many different size tubes. In the illustrated embodiment, the channel 602 generally has a truncated, circular, cross-sectional shape at its proximal end and distal end. In certain embodiments, the channel smoothly tapers in cross-sectional size from a smaller proximal end to a larger distal end. In such embodiments, the channel 602 generally has a truncated V-shape and preferably corresponds to the shape of the retained portion of the endo-tracheal tube 10 or medical device.

In the embodiment illustrated in FIGS. 21-25, the sides of the channel 602 are generally straight and parallel with each other. The walls of the channel 616 (and, thus, the grooves of the first portion 612 and second portion 614), however, need not be straight. For example, the wall of the first portion groove can have a convex section that narrows the portion of the channel so as to correspond in shape to the shape of the received portion of the endo-tracheal tube 10. This channel shape furthers retention of the endo-tracheal tube 10 within the channel 616 to inhibit endo-tracheal tube 10 movement through the channel, as discussed below.

Although the channel 616 can take the form of various shapes depending upon its application (i.e., depending upon a shape of the tube portion of the medical article for which the retainer is designed to be used), the channel 616 does have a sufficient length in the longitudinal direction to stabilize the endo-tracheal tube 10, rather than act as a fulcrum for the endo-tracheal tube 10. That is, the retainer 602 receives a sufficient length of the endo-tracheal tube 10 to inhibit movement of the endo-tracheal tube 10 in the lateral, longitudinal and transverse direction (i.e., to inhibit yaw, pitch and axial movement of the tube), without kinking the endo-tracheal tube 10.

When the first portion 612 is engaged with the second portion 614, a section of the endo-tracheal tube 10 is captured within the retainer 602. Thus, the retainer 602 at least restricts, if not prevents, lateral and transverse movement of the retained section of the endo-tracheal tube 10.

In certain embodiments, inhibiting movement of the endo-tracheal tube 10 in the longitudinal direction when the endo-tracheal tube 10 is secured within the channel 616 is desirably enhanced by one or more retention mechanisms associated with the contact area of the channel 616. One such retention mechanism involves the shape of the channel 616 itself. The interaction between the shape of the channel 616 and a corresponding shape of the endo-tracheal 10 may inhibit longitudinal movement.

The interaction between the contact area on the channel 616 and the endo-tracheal tube 10 creates friction to inhibit longitudinal movement through the channel 616. The degree of interference between the endo-tracheal tube 10 and the retainer 602, however, is preferably not so great as to significantly occlude the endo-tracheal tube 10.

Another retention mechanism to inhibit longitudinal movement of the endo-tracheal tube 10 involves one or more securement barbs 642 (see FIGS. 24 and 25) located on the contact area of the channel 616. The securement barbs 642 can be used to retain the endo-tracheal tube 10 in the longitudinal direction. In certain embodiments, each barb has a generally conical shape with a blunt tip. The barb may extend into the channel 616 by an amount ranging between about 0.1 mm and about 3 mm.

The securement barbs 642 may be arranged within the channel 616 to cooperate with one another. The barbs 642 advantageously are arranged within the same general lateral plane (i.e., a plane defined by the lateral and transverse axes), and are spaced apart from one another. In addition, the barbs 642 desirably are spaced on generally opposite contact areas on the channel 616 in a staggered arrangement. That is, the position of the barbs alternates between the first portion 612 and the second portion 614 in the lateral direction. The resulting overlapping pattern of the barbs securely holds the endo-tracheal tube 10 without imparting torque to the endo-tracheal tube 10 if pulled in a longitudinal direction.

Another retention mechanism to inhibit longitudinal movement of the endo-tracheal tube 10 involves one or more friction ridges located on the contact area of the channel 616.

The ridges may be integrally formed with the first and second portions and project into the channel 616. The ridges are desirably of smooth solid construction; however, they can be of hollow construction. The ridges can have generally triangular cross-sectional shapes and angle toward one or both ends of the channel 616. The ridges, however, can have other cross-sectional shapes which would interfere with longitudinal movement of the endo-tracheal tube 10 through the channel 616.

In certain embodiments having friction ridges, each of the ridges desirably has a front wall or leading edge that forms an angle of less than 90 degrees as measured between the front wall and the channel surface. The ridges slightly protrude into the channel 616, desirably at a transverse distance of between 0.1 to 10 mm for the given application. The ridges also lie generally normal to a longitudinal axis through the channel 616.

When so arranged, the friction ridges gently, but securely bite or press into an outer surface of the endo-tracheal tube 10. Such contact preferably does not significantly occlude or otherwise meaningfully impair air flow in the endo-tracheal tube 10 because of the compliant nature of the endo-tracheal tube 10 material and because of the degree to which the ridges bite into the endo-tracheal tube 10. This degree of contact, however, coupled with the angular orientation of the ridges inhibits movement of the endo-tracheal tube 10, especially in a direction opposite of that in which the ridges are angled.

Another possible retention mechanism to improve traction between the retainer 602 and the endo-tracheal tube 10 involves roughening the inside of the channel 616. The inside of the channel 616 can be roughened, or otherwise treated with a high friction coating to provide a better grip between the endo-tracheal tube 10 and retainer 602. This will help inhibit any undesired motion of the retainer 602 upon the endo-tracheal tube 10 once the retainer 602 is in position.

Another possible retention mechanism to inhibit axial movement of the endo-tracheal tube 10 relative to the retainer 602 involves an adhesive spot. An adhesive spot may be advantageously disposed upon the inside of the channel 616. The adhesive spot may take the form of a glue dot. Such glue dots are desirably formed of a material which exhibits high resistance to shear and which can be peeled off of the catheter without leaving a residue. Such an adhesive is sold by All-Pak Inc. of New Berlin, Wis. as part number GD-06 "Super High Tack Glue Dot." Multiple glue dots may be used, or a single glue dot may be disposed on only one side of the channel of the retainer 602. It is ordinarily not necessary for multiple glue dots to be used; a single glue dot disposed upon either the first or second portions may advantageously be used to provide greater frictional and transverse forces between the retainer 602 and the endo-tracheal tube 10.

Furthermore, the adhesive spot need not be a single point of adhesive. In certain embodiments, the adhesive spot is a region composed of an elastic and compressively deformable material such Kraton polymer compounds. Such a compound includes Dynaflex G2706 available from GLS Corporation, as well as other thermoplastic elastomers or silicone or urethane epoxies.

This region also need not be round. In certain embodiments, a large region of the surface of the channel 616 may be covered with a suitable material, such as Kraton. For instance, the entire channel surface on the first portion 612 might be covered with a thin layer of adhesive to advantageously provide additional traction and transverse bias between the endo-tracheal tube 10 and retainer 602.

Other means of producing an appropriate adhesive spot for use with various embodiments include without limitation: treating a portion of the surface of the channel chemically or electrically to adjust its surface friction or compressibility; spraying or spreading an adhesive coating onto a portion of the channel; attaching peel-off adhesive members to portions of the channel; injection molding regions of adhesive or compressible material, such as Kraton, to a portion of the surface of the channel; or such other means as are known in the art.

Figure 31:
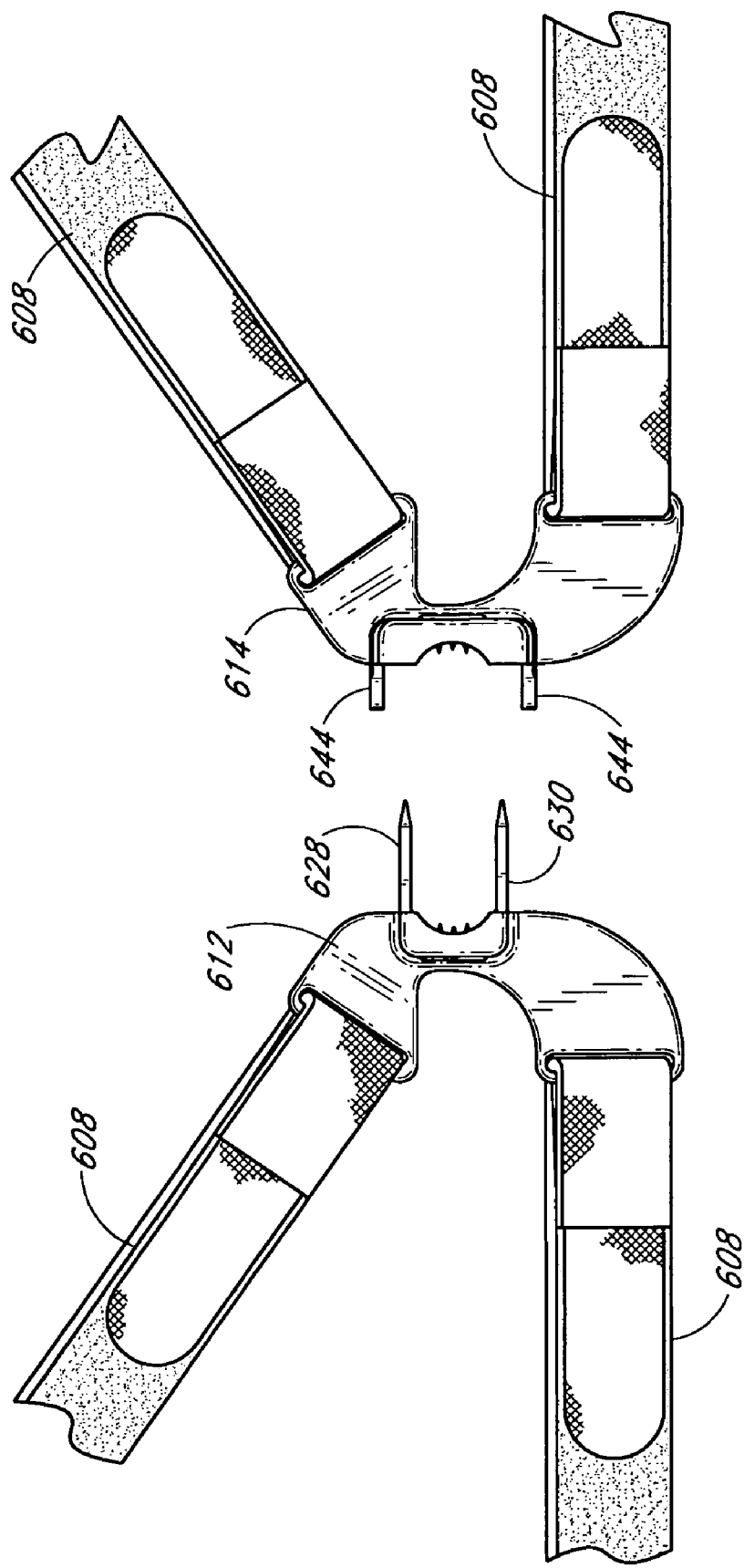
FIG. 31 illustrates a partial enlarged view of the securement system of FIG. 16 showing a plurality of attachment members attached to each of the first and second portions of the retainer at two locations.

FIG. 30 illustrates the use of the securement system 600 of FIG. 16 upon a patient. FIG. 31 illustrates a partial enlarged view of the securement system 600 of FIG. 16 showing a plurality of attachment members 608 attached to each of the first and second portions of the retainer 602 at two locations. A medical attendant can secure an endo-tracheal tube 10 (or other medical article) to a patient using the above-described securement system (or a readily apparent modification thereof). The medical attendant opens the retainer 602 to expose the grooves on the first and second portions 612, 614. The medical attendant places the patient's head on the head contact member 606 or brings the head contact member 606 in contact with the patient's head.

The medical attendant wraps the attachment members 608 around a portion of the patient's head and towards the patient's face. The first end portion of the attachment member 608 is attached to the retainer 602. Two attachment members 608 attach to the first portion 612 while two other attachment member 608 attach to the second portion 614. The second end portion of the attachment member 608 is attached to the securing regions 610 of the head contact member 606. Preferably, the attachment members 608 are attached to the head contact member 606 before being attached to the retainer 602.

With the retainer open, an endo-tracheal tube portion can be transversely aligned between the grooves in the retainer 602. The medical attendant generally aligns the first portion 612 with the second portion 614 as illustrated in FIG. 31 with the endo-tracheal tube 10 being located therebetween. Once the endo-tracheal tube 10 is so aligned and placed between or in a groove, the retainer is closed and latched by engaging the prongs 628, 630 of the first portion with the receptacle 634, 636 of the second portion 614. When in the closed position, the interengaging structure inhibits movement of the medical endo-tracheal tube 10 relative to the retainer 602.

If the retainer employs projections that clamp onto or pin the endo-tracheal tube 10 within the channel 616, then this engagement between the retainer and the endo-tracheal tube 10 would further secure the endo-tracheal tube 10 in place. If the endo-tracheal tube 10 is pulled in the distal direction, the securement barbs bite into the endo-tracheal tube 10 and also oppose movement of the endo-tracheal tube 10 in this direction.

The retainer 602 thus inhibits longitudinal movement of the endo-tracheal tube 10 relative to the retainer. The holding effect provided by each of the retention mechanisms, however, does not significantly occlude the endo-tracheal tube 10. And although the securement barbs bear against the endo-tracheal tube 10, their limited bite does not significantly occlude or penetrate the endo-tracheal tube 10.

The retainer 602 can include only one retention member or possibly several; it need not include any at all. In addition, any combination of the retention members (for example, an adhesive spot and secure barbs) in the retainer is also possible.

When in place, the lower two attachment members 608 are disposed beneath the ears, while the upper two attachment members 608 are above the ears and cross over the temples of the patient. Further, the lower two attachment members 608 are attached to the retainer 602 below the lip line while the upper two attachment members 608 are attached to the retainer 602 above the lip line.

Figure 32:
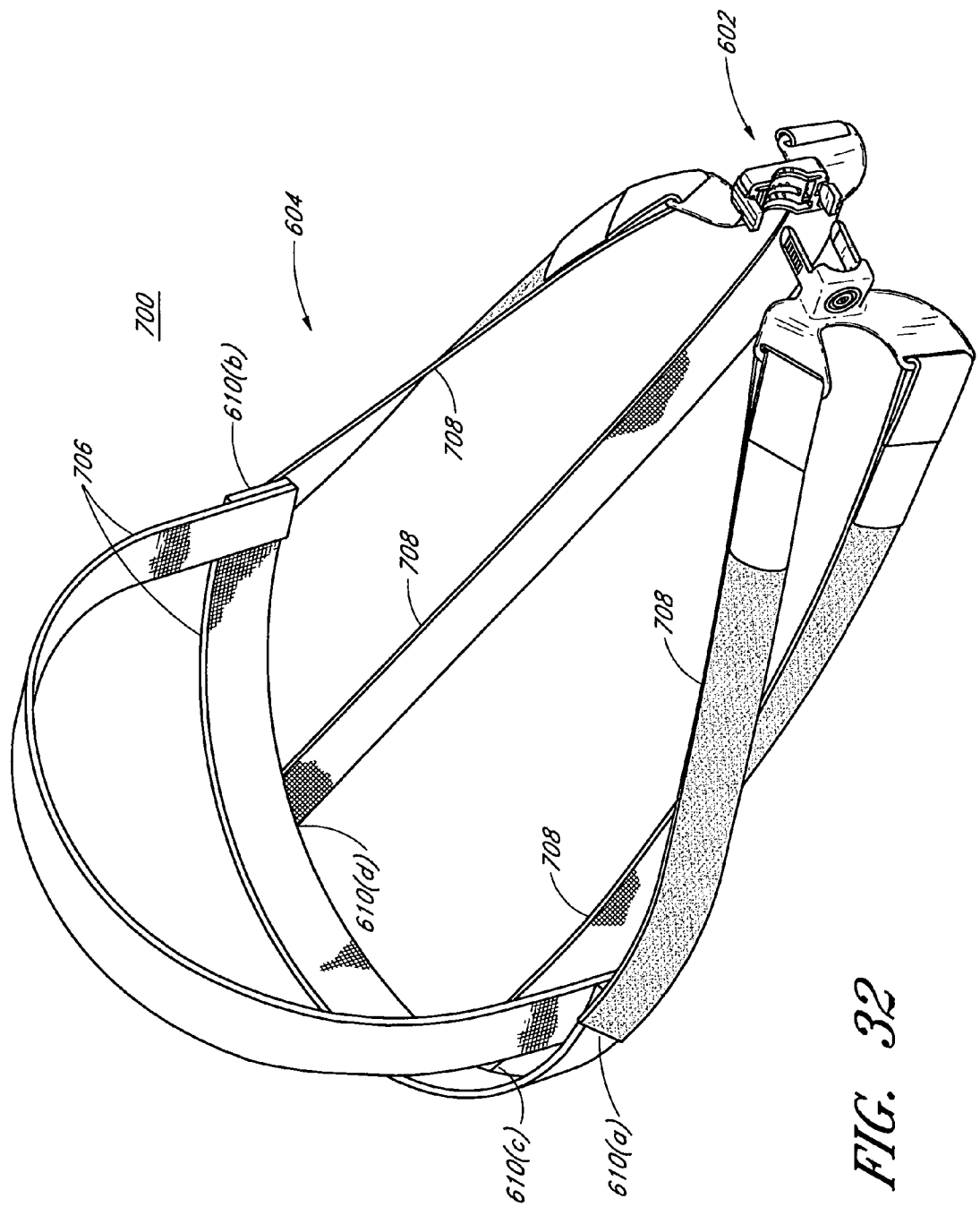
FIG. 32 illustrates another embodiment of a securement system in accordance with the present invention.
Figure 33:
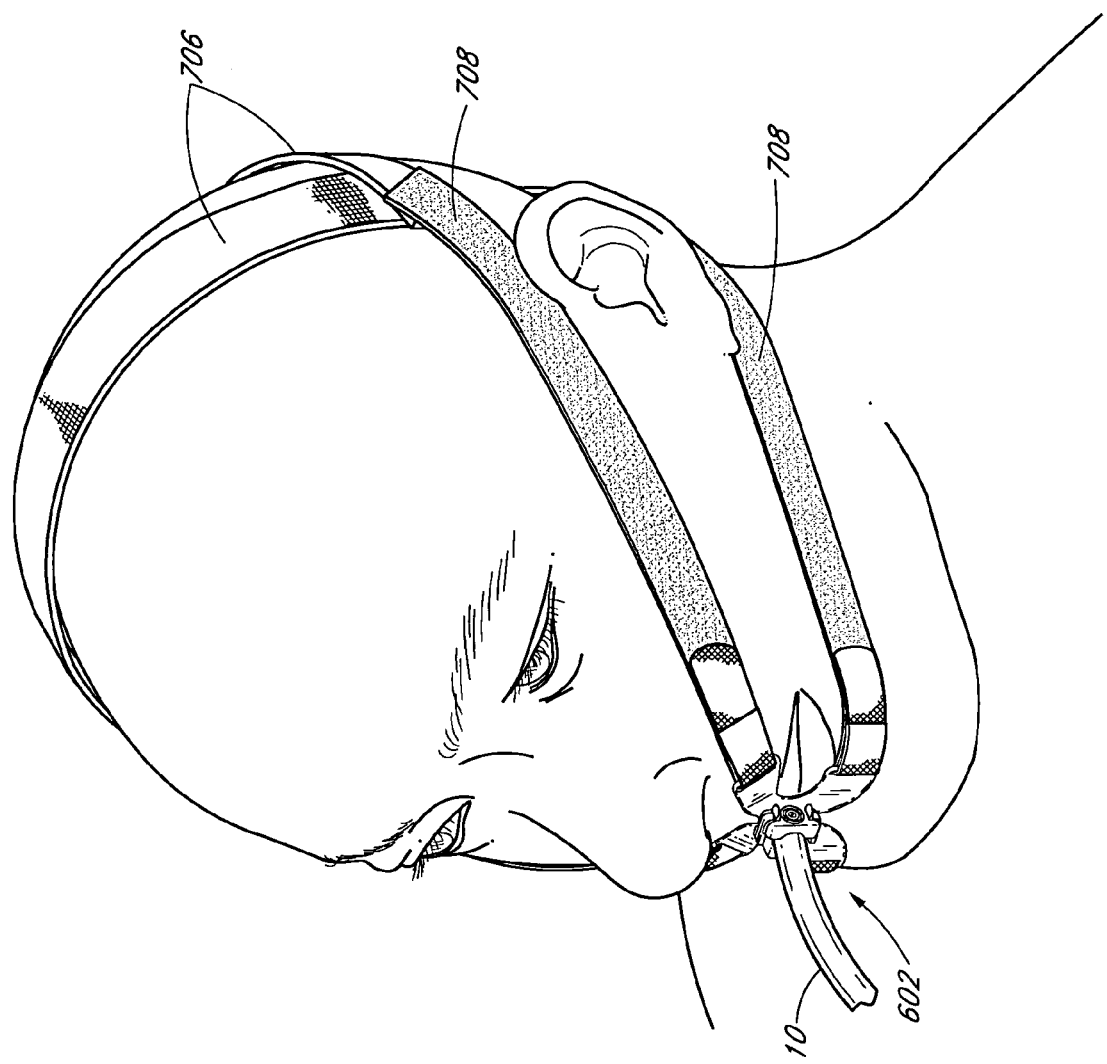
FIG. 33 illustrates the use of the securement system of FIG. 32 upon a patient.

FIG. 32 illustrates another preferred embodiment of a securement system 700. FIG. 33 illustrates the use of the securement system 700 of FIG. 32 upon a patient. The securement system 700 includes a retainer 602 which is secured upon the face of a patient by a harness 604. The harness 604 retains the retainer 602 in the operative position to support an endo-tracheal tube. The illustrated retainer 602 is the same retainer described with reference to FIGS. 19-29. The harness 604 is similar to the harness described with reference to FIG. 16 except that the head contact member 606 illustrated in FIG. 16 is made of interconnected straps in the embodiment illustrated in FIG. 32. Further, the attachment members 708 are similar to the attachment member 608 except that the second ends are preferably integral with the strap head contact member 706.

While not illustrated in FIGS. 16 and 32, the first end portion of the attachment members 608, 708 may be integral with the retainer 602 and the second end portion of the attachment members 608 may be integral with the head contact member 606. In embodiments having integral or fixed first or second ends, the attachment members 608, 708 may comprise an elastic material which keeps the attachment members 608, 708 taut between the back of the patient's head and the retainer 602 by stretching the attachment members 608, 708. Alternatively or in combination with an elastic portion, the attachment members 608, 708 may include adjustment means for changing the length of the attachment members 608, 708 between the integral or fixed first or second ends. The adjustment means may be a mechanical system which allows the medical attendant to change the length of the attachment members 608, 708 between the head contact member 606, 706 and the retainer 602. Other adjustment means include but are not limited to: snaps, clips, Velcro, or such other fasteners as are known to those of skill in the art.

In the exemplary embodiment illustrated in FIG. 32, the strap head contact member 706 includes securing regions 610a, 610b, 610c, 610d. The securing regions 610 integrally attach the attachment members 708 to the strap head contact member 706.

Each attachment member 708 comprises a first end portion and a second end portion. In certain embodiments, the first end portion has a hook and loop fastener. The first end portion is configured for attachment to the securing locations 618 of the retainer 602 (see FIG. 19). The second end portion of the attachment member 708 is configured for attachment to the securing regions 610 of the strap head contact member 706. In certain embodiments, at least a portion of each attachment member 708 comprises a flexible material. For example, the attachment member 708 may comprise VELSTRETCH made by Velcro USA Inc. located in New Hampshire.

Figure 35:
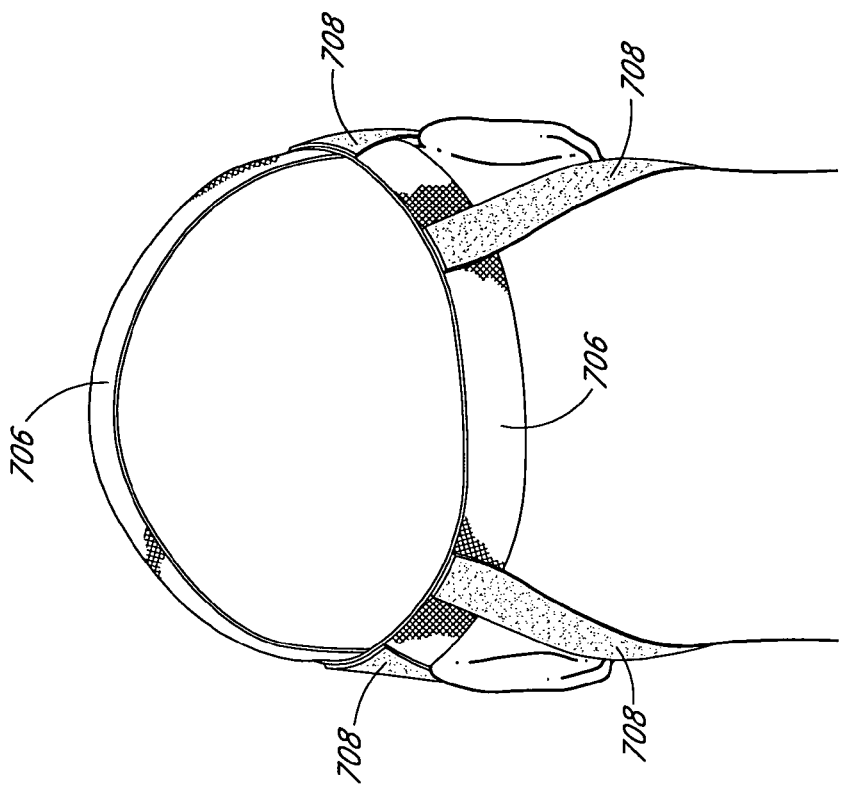
FIG. 35 illustrates the use of the securement system of FIG. 32 upon a patient and shows the strap head contact member encircling at least a portion of the patient's skull.

The harness 604 which secures the retainer 602 to the patient's face for use includes a strap head contact member 706 which generally encircles at least a portion of the patient's skull as illustrated in FIG. 35. In certain embodiments, the strap head contact member 706 has the shape of a closed loop and is sized to receive a portion of the skull of a patient. In certain embodiments, the strap head contact member 706 encircles the lambda of the patient's skull. In certain embodiments, the strap head contact member 706 spans across at least the sagittal suture of the patient's skull. In preferred embodiments, when positioned with the attachment members 708 in tension, the head contact member 706 exerts pressure on the occipital bone, and preferably also on the parietal bone.

Preferably, the loop of the strap head contact member 706 is smaller than the patient's skull and restricts the skull from passing entirely through the center of the loop. While the illustrated embodiment of the strap head contact member 706 has a fixed sized opening, in certain embodiments the strap head contact member 708 includes overlapping ends having suitably, infinitely adjustable fastening means, such as hook and loop fasteners (e.g., VELCRO, fastener pads) whereby the strap head contact member 706 may be adjusted to firmly and snuggly encompass a portion of the patient's head.

In certain embodiments, the strap head contact member 706 includes a middle strap (not shown) which extends across the center opening of the strap head contact member 706.

For embodiments having an integral harness 604 and attachment members 708, the first end portions of the attachment members 708 are adjusted to fit the securement system to the patient. The described harness 604 provides for firm securement of the retainer 602 in its use position by means of an adjustable fit whereby the patient's head movement or external manipulation of the endo-tracheal tube 10 result in minimal disturbance of the endo-tracheal tube 10 in the patient's airway.

Figure 34:
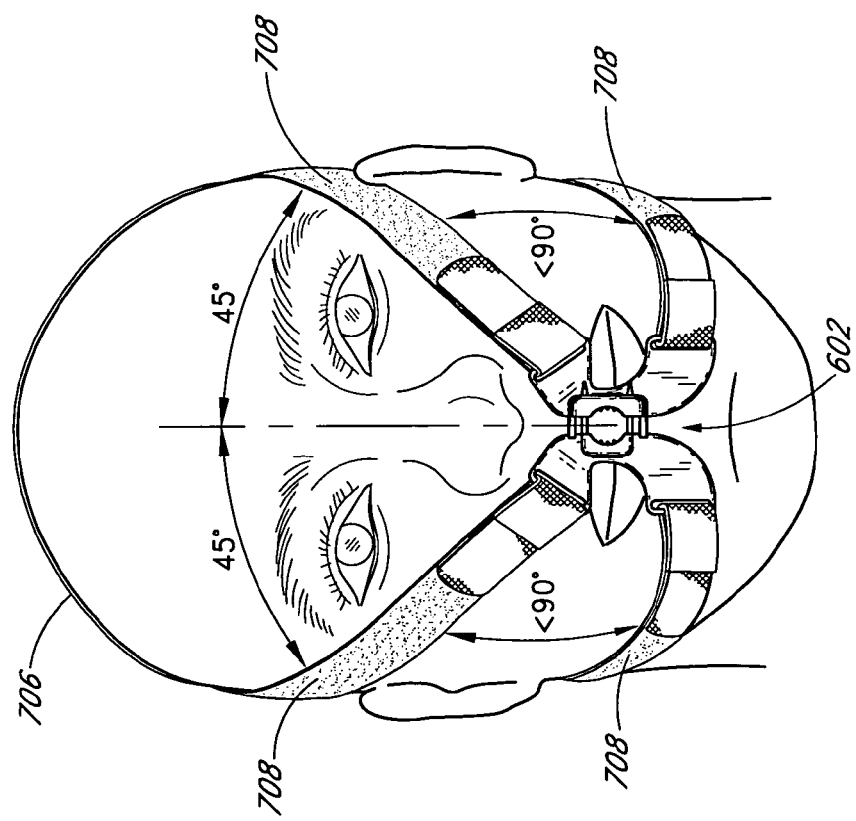
FIG. 34 illustrates the use of the securement system of FIG. 32 upon a patient and shows the attachment members aligned with the securing locations of the retainer.

FIGS. 34 and 35 illustrate the use of the securement system of FIG. 32 upon a patient. FIG. 34 shows the upper attachment members 708 aligned with the retainer 602 and spaced 90 degrees apart and the lower attachment members 708 aligned with the retainer 602 and spaced 90 degrees apart to ease access to the sides of the mouth while providing stability to the retainer 602 on the patient's face. FIG. 35 shows the strap head contact member 708 encircling at least a portion of the patient's skull.

In FIG. 34, the opposing concave sections of the anchor feet 626, 632 (see FIGS. 19 and 23) create a notch or cutout proximate to the center of the retainer 602. As a result, the notched regions of the anchor feet 626, 632 provide clearance to access the sides of the patient's mouth for oral care and other nursing care as required. The outwardly extending wide regions of the anchor feet 626, 632 provide stability on the patient's mouth. As illustrated in FIG. 34, the posterior facing surface 620 of the retainer is disposed superior and inferior relative to the midline of the lips.

Figure 36:
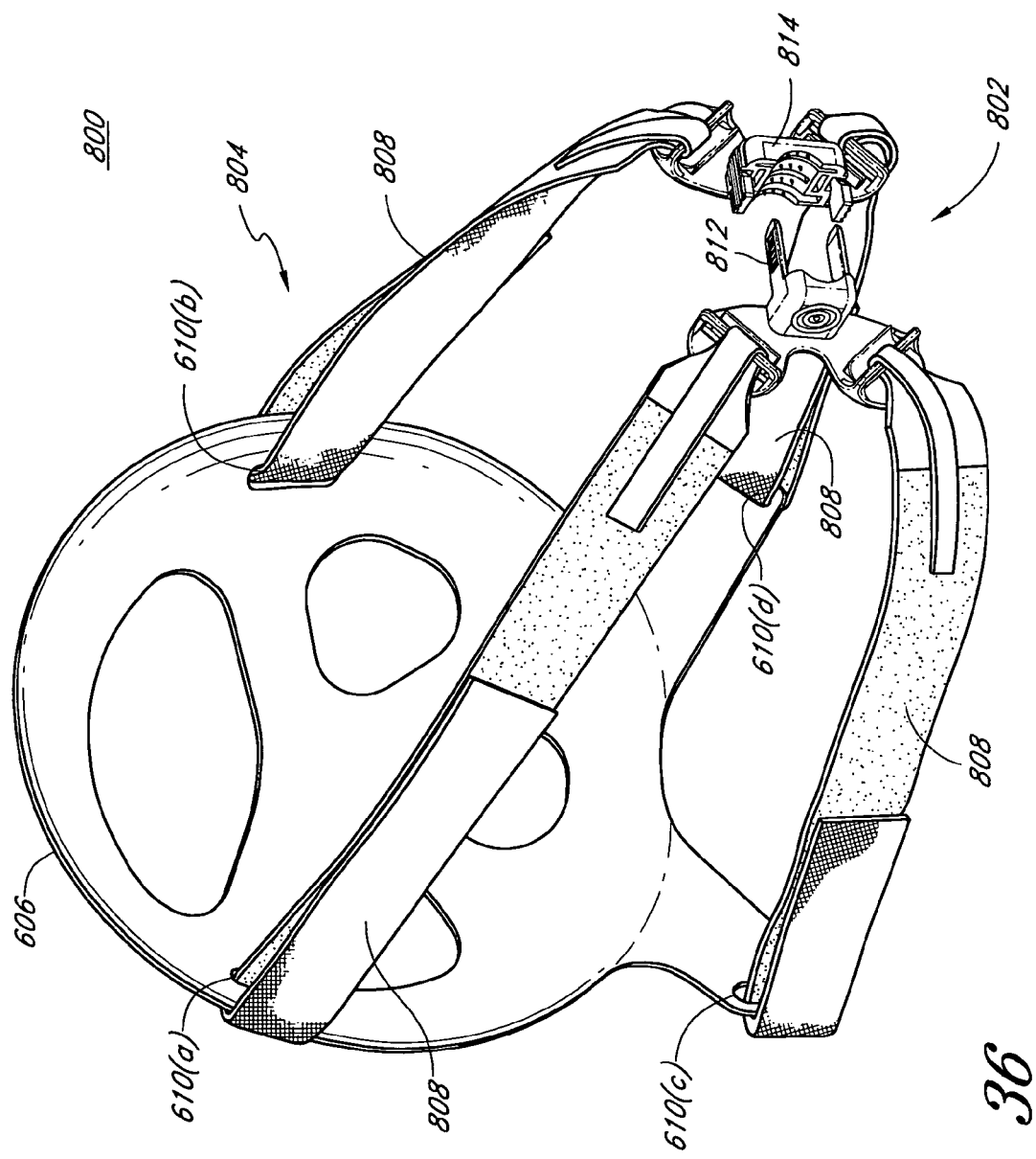
FIG. 36 illustrates another embodiment of a securement system in accordance with the present invention.

FIG. 36 illustrates another preferred embodiment of a securement system 800. The embodiment illustrated in FIGS. 36 through 47 is similar to the embodiment described with reference to FIGS. 16 through 31 except that the embodiments of the retainers 602, 802 and of the attachment members 608, 808 are not the same. Furthermore, the attachment members 608, 808 attach differently to the retainers 602, 608 for the different embodiments. Features and structure similar to both embodiments are identified with the same last two digits (for example, 608 and 808) for ease of explanation. Thus, the detailed description for features of the securement system 600 applies with equal force to the similar features found in the securement system 800.

The securement system 800 includes a retainer 802 which is secured upon the face of a patient by a harness 804. The harness 804 which secures the retainer 802 to the patient's face includes a head contact member 606 and attachment members 808 for use in the described securement system 800.

Each attachment member 808 comprises a first end portion and a second end portion. In certain embodiments, the first end portion has a hook and loop fastener. The first end portion is configured for attachment to the retainer 802. The second end portion of the attachment member 808 is configured for attachment to the securing regions 610 of the head contact member 606.

The retainer 802 comprises a first portion 812 and a second portion 814. The first portion 812 is configured to engage with the second portion 814 forming a tubular channel 816 therebetween (see FIG. 37). The channel 816 is configured to receive a portion of the endo-tracheal tube 10 so as to inhibit movement of the endo-tracheal tube 10 relative to the retainer 802.

Figure 37:
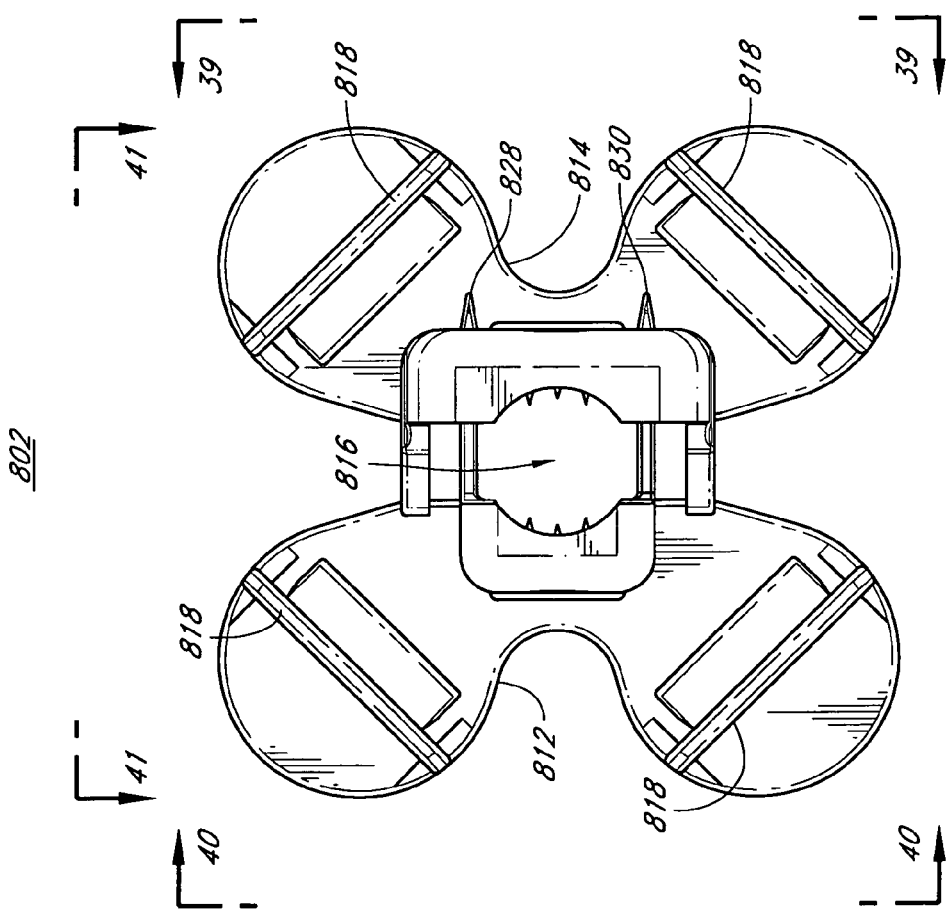
FIG. 37 illustrates a top view of a retainer of the securement system of FIG. 36.

The retainer includes a plurality of securing locations 818 located on the first and second portions 812, 814 (see FIG. 37). Each of the first and second portions 812, 814 comprises at least one securing location 818. The securing locations 818 are configured for attachment to the first ends of the attachment members 808. The width of the securing location 818 may be sized to accommodate the width of the attachment member 808. For example, the width of the attachment member 808 can be equal to or less than the width of the securing location 818 to facilitate threading of the first end around the securing location 818. In the illustrated embodiment, the width of the attachment member 808 necks down near the first end. In certain embodiments, the securing locations 818 are located superior and inferior to the lips of the patient when the retainer 802 is placed upon the patient's mouth.

To facilitate attachment of the attachment members 808, the first and second portions 812, 814 may include ramps 846 (see FIGS. 44-47). The ramps 846 provide a curved surface to preferentially direct the first end of the attachment member 808 around the securing location 818 when assembling the securement system 800.

A posterior facing surface faces the head contact member 806 when worn by a patient and is configured to inhibit longitudinal movement of the retainer 802 into a patient's mouth. In certain embodiments, the posterior facing surface 820 is disposed superior and inferior relative to the midline of the lips so as to allow access to the sides of the mouth.

Figure 38:
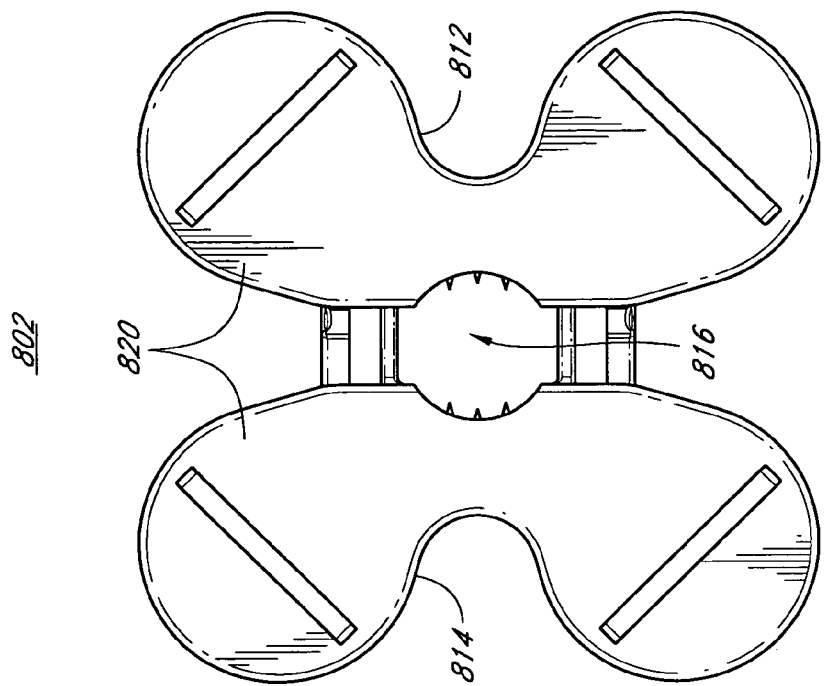
FIG. 38 illustrates a bottom view of the retainer of the securement system of FIG. 36.

FIG. 37 illustrates a top view of a two piece retainer 802 of the securement system of FIG. 36. FIG. 38 illustrates a bottom view of the retainer 802. The retainer 802 fastens or connects to the endo-tracheal tube 10. The securing locations 818 attach to the attachment members 808.

FIG. 39 illustrates a side view of the retainer of FIG. 37 having a first finger pressure surface 822. FIG. 40 illustrates an opposite side view of the retainer of FIG. 37 having a second finger pressure surface 824. The first and second finger surfaces 822, 824 provide regions for a medical attendant to squeeze the first portion 812 and the second portion 814 together to form the retainer 802.

FIG. 41 illustrates a side view of the two-piece retainer of FIG. 37 with a first portion 812 engaged with a second portion 814. Each of the first and second portions 812, 814 is a one-piece molding of plastics material. Each portion 812, 814 includes a groove as described below.

Figure 45:
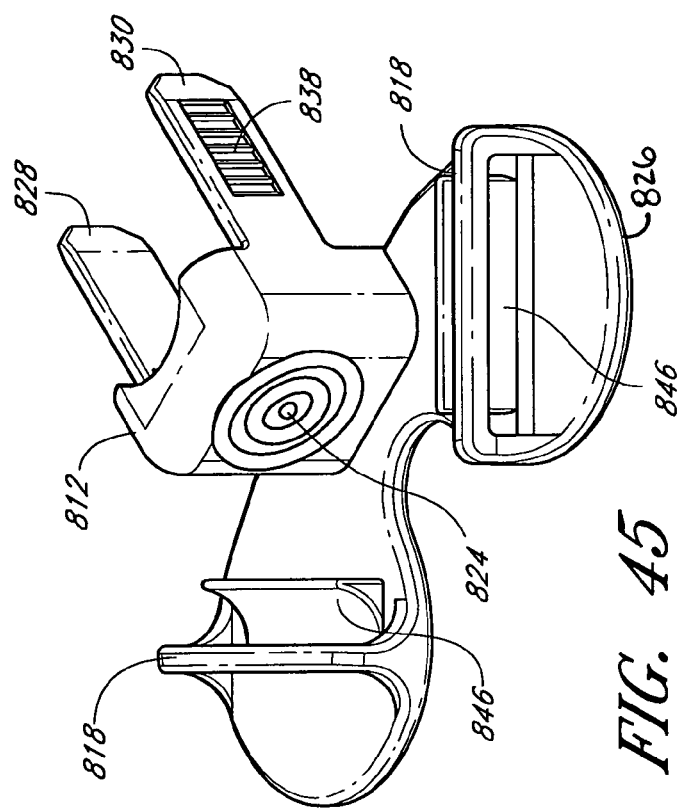
FIG. 45 illustrates an opposite side perspective view of the first portion of the retainer of FIG. 44.
Figure 44:
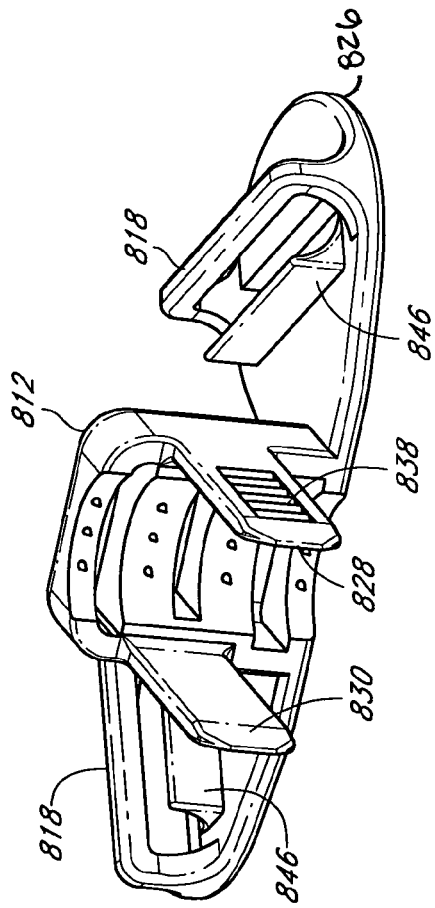
FIG. 44 illustrates a perspective view of a first portion of the retainer of FIG. 37.

FIGS. 44 and 45 illustrate perspective views of a first portion 812 of the retainer of FIG. 37. The first portion 812 comprises an anchor foot 826, a pair of transversely extending parallel flexible prongs 828, 830, and the securing locations 818. The prongs 828, 830 are preferably integrally formed with the first portion 812.

Figure 47:
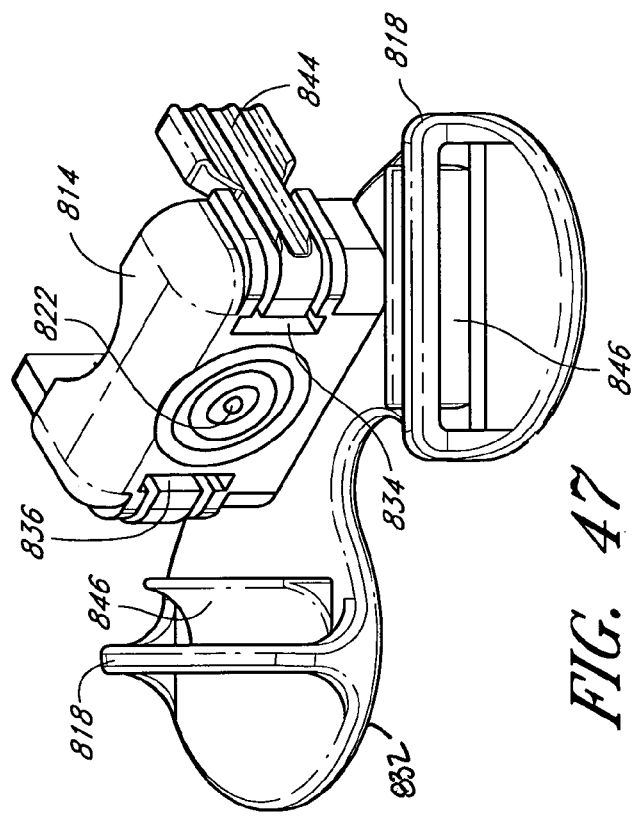
FIG. 47 illustrates an opposite side perspective view of the second portion of the retainer of FIG. 46.
Figure 46:
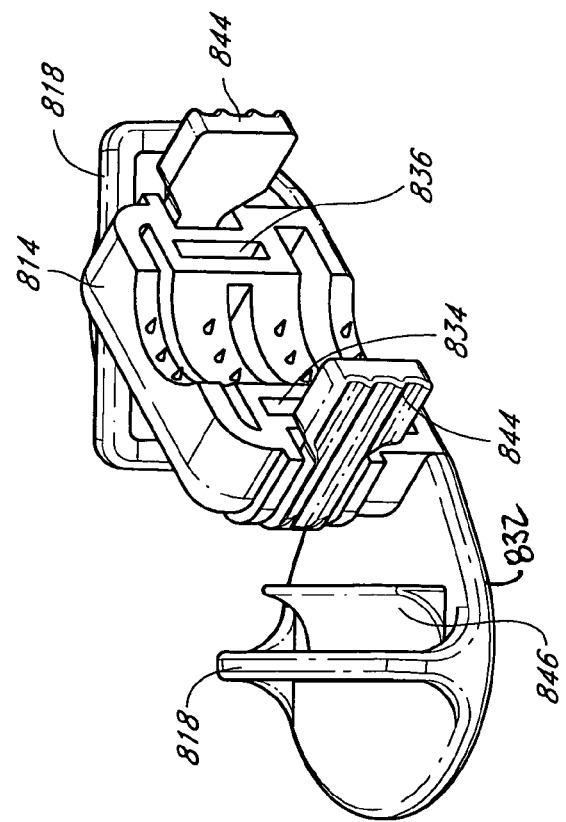
FIG. 46 illustrates a perspective view of a second portion of the retainer of FIG. 37.

FIGS. 46 and 47 illustrate perspective views of a second portion 814 of the retainer of FIG. 37. The second portion 814 comprises an anchor foot 832, a pair of transversely extending parallel receptacles or apertures 834, 836, and securing locations 818. The receptacles 834, 836 are configured to receive the prongs 828, 830 of the first portion 812. In the illustrated embodiment, the anchor feet 826, 832 (see FIGS. 37 and 41) desirably include a pair of opposing concave sections that narrow the center of the anchor feet 826, 832 proximate to the center of the retainer 802.

The two portions 812, 814 are adapted to be engaged, as shown in FIG. 37, to form a tubular channel 816 therebetween for receiving the endo-tracheal tube 10. Once engaged, the first and second portions are laterally slidable together so as to reduce the channel 816 cross-section and firmly grip the endo-tracheal tube 10. The first and second portions are inhibited from sliding apart by interengaging structure as described below.

Figure 43:
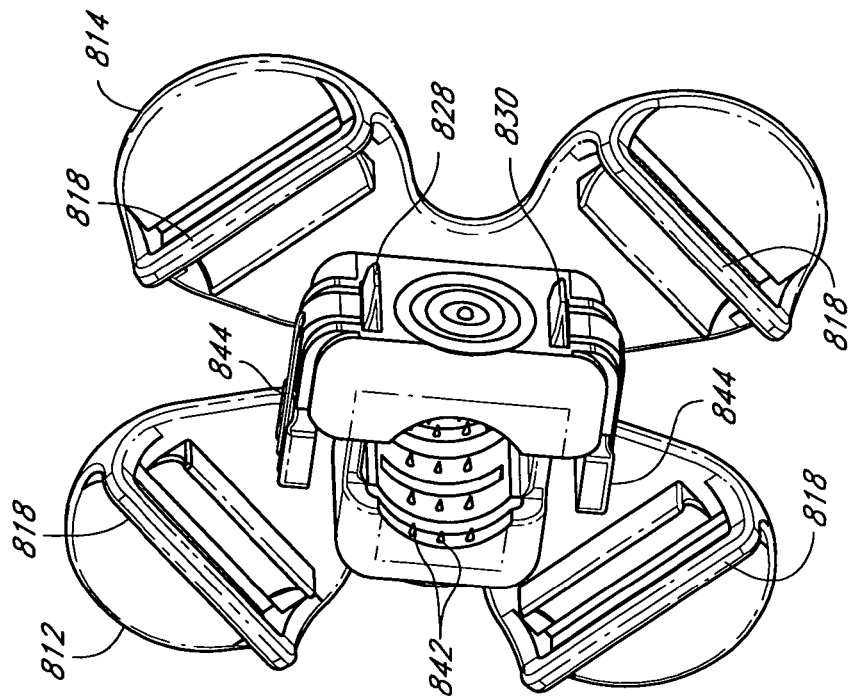
FIG. 43 illustrates an opposite side perspective view of the retainer of FIG. 37.
Figure 42:
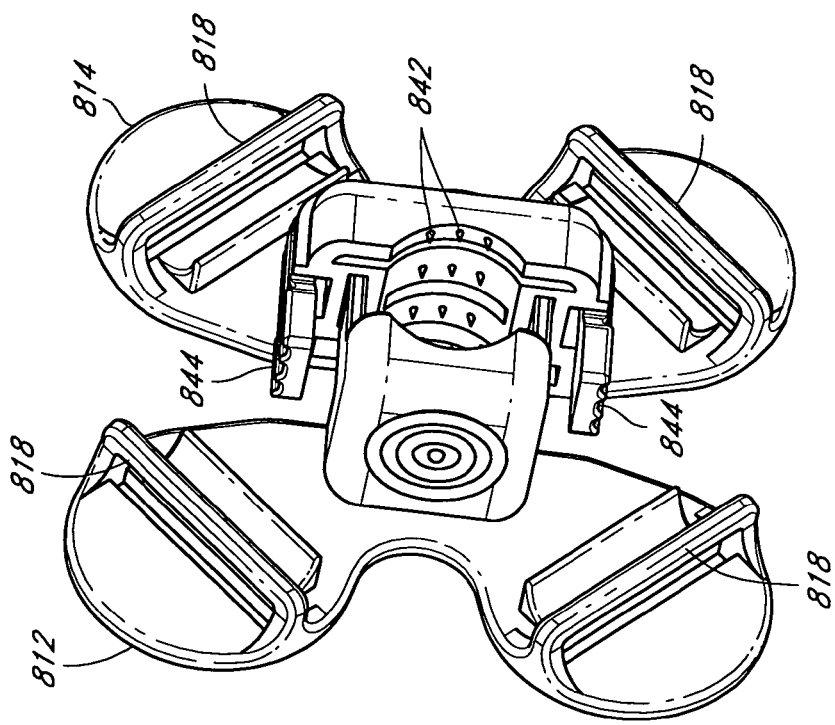
FIG. 42 illustrates a perspective view of the retainer of FIG. 37.

The channel 816 is formed by respective hemispherical grooves in the portions 812, 814. As best seen in FIGS. 42 and 43, the grooves have a consistent width along the longitudinal axis. In certain embodiments, the grooves vary in width (i.e., in the lateral direction) along their longitudinal lengths.

To firmly hold the endo-tracheal tube 10 within the channel 816, the retainer 802 includes interengaging structure. The interengaging structure inhibits the first portion 812 and second portion 814 from slidingly disengaging from one another. The interengaging structure may be releasable or not.

In the illustrated embodiment and as best seen in FIGS. 44-47, the interengaging structure is a releasable latch mechanism. The latch mechanism is used to secure the first portion 812 to the second portion 814. In the illustrated embodiment, the latch mechanism comprises interfitting teeth 838 (see FIGS. 44 and 45) provided on prongs 828, 830 and a pair of receptacles 834, 836 (see FIGS. 46 and 47) of complementary shape to the prongs. Each receptacle 834, 836 includes an inner edge which locks with the teeth 838 on the prong 828, 830. The inner edges of the receptacles 834, 836 snap against the teeth 838 when the prongs 828, 830 are inserted through the receptacles 834, 836 forming the closed position.

In FIG. 39 the prongs 828, 830 are shown inserted through the receptacles 834, 836. The prongs 828, 830 interact with the receptacles 834, 836 formed in the second portion 814 to secure the prongs 828, 830 in their operative positions inhibiting the first portion 812 from moving away from the second portion 814.

FIGS. 42 and 43 illustrate perspective views of the retainer 802 of FIG. 37. As seen in FIG. 43, prongs 828, 830 have been inserted through receptacles 834, 836 and the prong teeth 838 engage with corresponding edges or teeth on the second portion 814 to clamp the endo-tracheal tube 10 in place within the channel 816.

For embodiments having releasable interengaging structure, the interengagement is released to allow the retainer portions 812, 814 to be separated, thereby permitting removal and replacement of an endo-tracheal tube 10 within the channel 816 of the retainer 802. In certain embodiments, a medical attendant presses downward on platforms 844 (see FIGS. 42 and 43) to disengage the prongs 828, 830 from the inner edges and slides the first portion 812 away from the second portion 814.

Securement barbs 842, adhesive spots, surface treatments, and friction ridges can be used to retain the endo-tracheal tube 10 in the longitudinal direction. The retainer can include only one retention member or possibly several; it need not include all. In addition, any combination of the retention members (for example, an adhesive spot and secure barbs) in the retainer is also possible.

Figure 48:
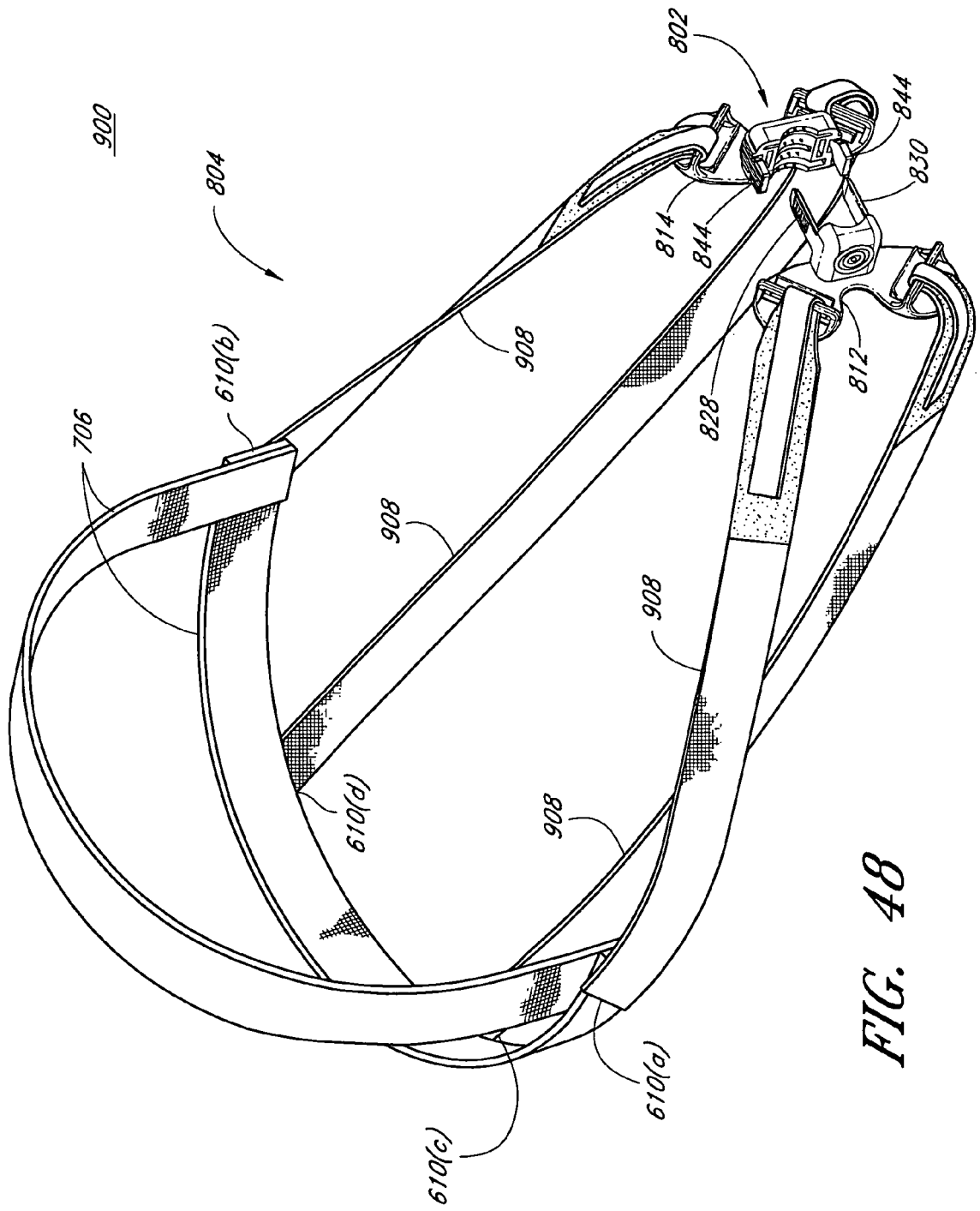
FIG. 48 illustrates another embodiment of a securement system in accordance with the present invention.

FIG. 48 illustrates another preferred embodiment of a securement system 900. The securement system 900 includes a retainer 802 which is secured upon the face of a patient by a harness 804. The illustrated retainer 802 is the same retainer described with reference to FIGS. 37-47. The harness 804 is similar to the harness described with reference to FIG. 32-35 except that the width of the attachment members 908 illustrated in FIG. 48 necks down near the first end. Similar features and structure to the embodiments are identified with the same last two digits (for example, 708 and 908) for ease of explanation. Thus, the detailed description for features of the securement systems 700, 800 applies with equal force to the similar features found in the securement system 900.

In the exemplary embodiment illustrated in FIG. 48, the strap head contact member 706 includes securing regions 610a, 610b, 610c, 610d. The securing regions 610 integrally attach the attachment members 908 to the strap head contact member 706.

Each attachment member 908 comprises a first end portion and a second end portion. The first end portion is configured for attachment to the securing locations 818 of the retainer 802. The second end portion of the attachment member 908 is configured for attachment to the securing regions 610 of the strap head contact member 706.

Figure 50:
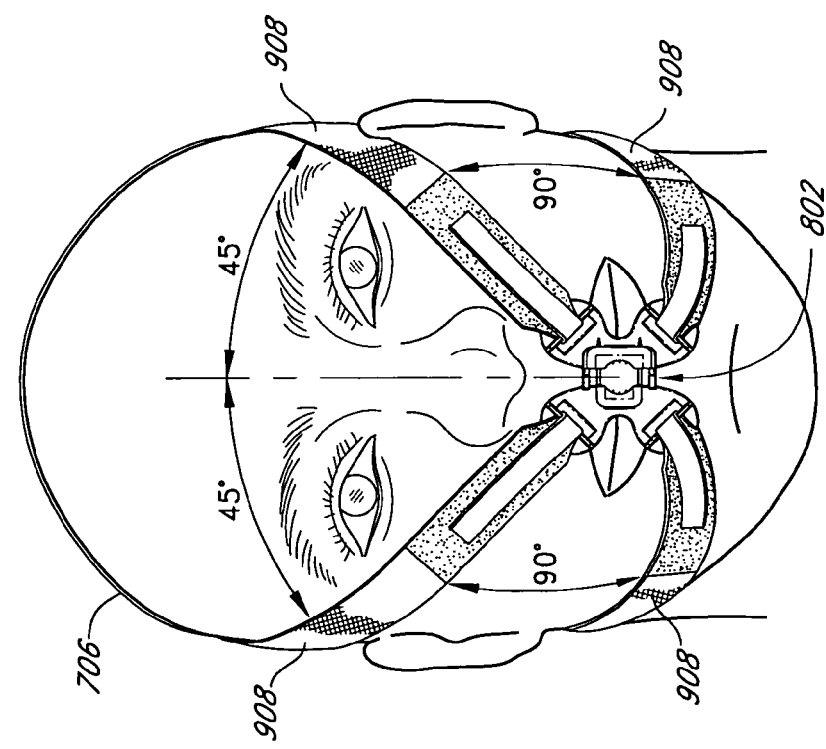
FIG. 50 illustrates the use of the securement system of FIG. 48 upon a patient and shows the strap head contact member encircling at least a portion of the patient's skull.

The harness 804 which secures the retainer 802 to the patient's face for use includes a strap head contact member 706 which generally encircles at least a portion of the patient's skull as illustrated in FIG. 50. In certain embodiments, the strap head contact member 706 has the shape of a closed loop and is sized to receive a portion of the skull of a patient. In certain embodiments, the strap head contact member 706 encircles the lambda of the patient's skull. In certain embodiments, the strap head contact member 706 spans across at least the sagittal suture of the patient's skull.

Figure 49:
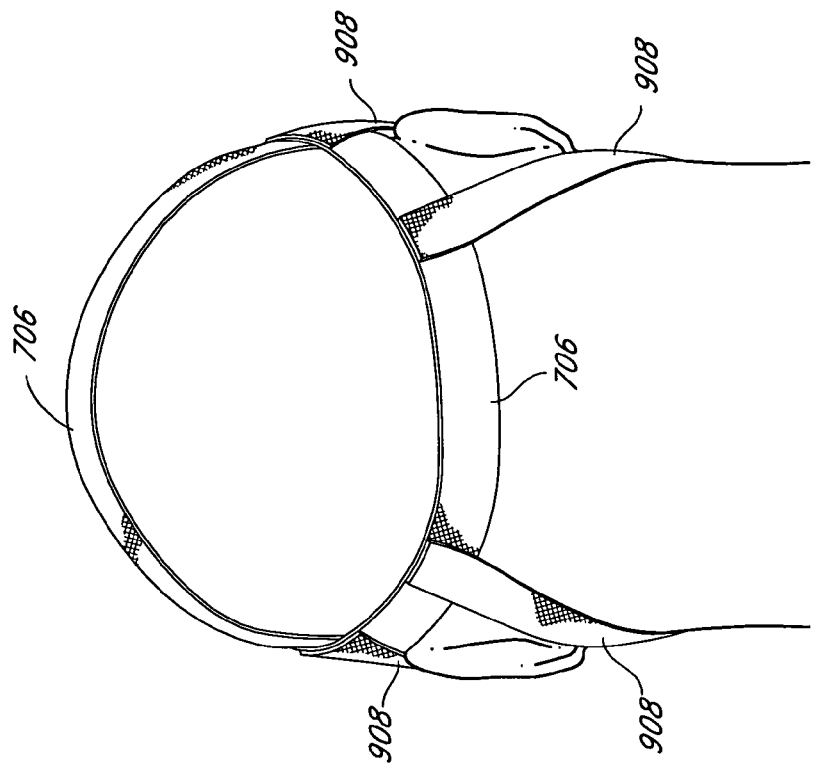
FIG. 49 illustrates the use of the securement system of FIG. 48 upon a patient and shows the attachment members aligned with the securing locations of the retainer.

FIGS. 49 and 50 illustrate the use of the securement system of FIG. 48 upon a patient. FIG. 49 shows the attachment members 908 aligned with the retainer 802 and spaced 90 degrees apart to ease access to the sides of the mouth while providing stability to the retainer 802 on the patient's face. FIG. 50 shows the strap head contact member 908 encircling at least a portion of the patient's skull.

The various embodiments of the securement systems described above in accordance with the present invention thus provide a means to secure an endo-tracheal tube or other medical article to a patient releasably. The endo-tracheal tube 10 can be adjusted without removing the entire securement assembly, and without the need for use of additional tape to re-secure the endo-tracheal tube 10 once it is properly repositioned. In addition, the retainer can be configured to be used with any of a wide variety of tubes and other medical articles. The securement system inhibits both inward and outward migration of the endo-tracheal tube 10 within the patient, and allows for access to the oral cavity of the patient in order to allow appropriate mouth care to take place.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct securement systems and techniques in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A securement system comprising:
a retainer for retaining an endo-tracheal tube, the retainer having surfaces configured to contact skin proximate to a patient's mouth to inhibit movement of the retainer and endo-tracheal tube into the patient's mouth, the surfaces being disposed superior and inferior relative to the midline of the lips so as to allow access to the sides of the mouth, the retainer having attachment locations for attaching the retainer to securement members, at least one of the attachment locations being movable with respect to at least another of the attachment locations, and at least one of the attachment locations being superior to the lips and at least another of the attachment locations inferior to the lips.

2. The system of claim 1, wherein the retainer further comprises a channel configured to receive a portion of the endo-tracheal tube so as to inhibit movement of the endo-tracheal tube relative to the retainer.

3. The system of claim 1, wherein the retainer further comprises a pad attached to at least a portion of the surfaces and configured to contact the patient's mouth.

4. The system of claim 2, wherein the retainer comprises a first portion and second portion, the attachment locations being located on the first and second portions.

5. The system of claim 4, wherein the first portion is configured to engage with the second portion, the first and second portions forming the channel.

6. The system of claim 4, wherein the first portion is configured to releasably engages with the second portion.

7. The system of claim 1, wherein the attachment locations ate sized to accommodate the securement members.

8. The system of claim 7, wherein a width of the attachment locations is equal to or less than a width of the securement members.

9. The system of claim 1, wherein at least a portion of the securement members narrows in width to facilitate attachment to the attachment locations.

10. The system of claim 1, wherein the retainer further comprises ramps to facilitate attachment of the securement members.

11. The system of claim 10, wherein the ramps include a curved surface to preferentially direct the securement members around the attachment locations.

12. The system of claim 1, wherein the attachment locations include a bar member, the securement members being configured to wrap around the bar member.

13. The system of claim 1, wherein the attachment locations include a passage configured to receive the securement members.

14. The system of claim 13, wherein the attachment locations are arranged such that a plane across an opening to the passage is perpendicular to a posterior surface of the retainer.

15. A method comprising:
placing a head contact member on a patient's head, the head contact member being in contact with a plurality of securing straps;
wrapping the plurality of securing straps around a portion of the patient's head, the plurality of straps being in contact with a retainer having a first portion and a second portion, at least one of the plurality of straps being in contact with the first portion and at least another of the plurality of straps being in contact with the second portion;
generally aligning the first portion with the second portion on opposite sides of a medical tube; and engaging the first portion with the second portion so as to inhibit movement of the medical tube relative to the retainer.

16. The method of claim 15, further comprising adjusting the length of the securing straps so as to secure the medical tube to the head contact member.

17. The method of claim 15, further comprising locating the retainer against the lips of the patient.

18. The method of claim 15, wherein the head contact member encircles at least the lambda of the patient's head, and wherein the head contact member is sized to prevent the patient's head from passing through the head contact member.

19. The method of claim 15, wherein the head contact member is sized such that a central portion, when positioned on the patient's head with the plurality of straps in tension, places pressure on an occipital bone of the patient.

20. The method of claim 19, wherein the central portion places pressure on a parietal bone of the patient.

21. A method comprising:
providing a plurality of securing straps, each having a first end and a second end, the first end contacting a head contact member and the second end contacting a retainer, wherein the retainer comprises a first portion and a second portion, at least one of the plurality of securing straps being in contact with the first portion and at least another of the plurality of securing straps being in contact with the second portion;
contacting the head contact member to a patient's head;
wrapping the plurality of securing straps around at least a portion of the patient's head;
generally aligning the first portion with the second portion on opposite sides of the medical tube;
engaging the first portion to the second portion so as to inhibit movement of the medical tube relative to the retainer; and
separating the plurality of securing straps for placement on both sides of the patient's head.

22. The method of claim 21, further comprising adjusting the length of one or more of the plurality of securing straps so as to secure the medical tube to the head contact member.

23. A securement system comprising:
a retainer for retaining an endo-tracheal tube, the retainer having surfaces configured to contact skin proximate to a patient's mouth to inhibit movement of the retainer and endo-tracheal tube into the patient's mouth, the surfaces being disposed superior and inferior relative to the midline of the lips so as to allow access to the sides of the mouth, the retainer having attachment locations for attaching the retainer to securement members, at least one of the attachment locations being superior to the lips and at least another of the attachment locations inferior to the lips, wherein the retainer further comprises ramps to facilitate attachment of the securement members.

* * * * *

UNITED STATES PATENT AND TRADEMARK OFFICE
CERTIFICATE OF CORRECTION

PATENT NO. : 7,568,484 B2  Page 1 of 1
APPLICATION NO. : 11/303454
DATED : August 4, 2009
INVENTOR(S) : Bierman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 294 days.

Signed and Sealed this

Seventh Day of September, 2010

David J. Kappos
*Director of the United States Patent and Trademark Office*